(12) United States Patent
Predick et al.

(10) Patent No.: US 11,337,825 B2
(45) Date of Patent: May 24, 2022

(54) STEERABLE IMPLANT ASSEMBLY

(71) Applicant: LIFE SPINE, INC., Huntley, IL (US)

(72) Inventors: Daniel P. Predick, West Lafayette, IN (US); Madeline Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 16/875,465

(22) Filed: May 15, 2020

(65) Prior Publication Data

US 2021/0353428 A1    Nov. 18, 2021

(51) Int. Cl.
*A61F 2/44* (2006.01)
*A61F 2/30* (2006.01)

(52) U.S. Cl.
CPC .... *A61F 2/4425* (2013.01); *A61F 2002/3055* (2013.01); *A61F 2002/30578* (2013.01); *A61F 2002/443* (2013.01)

(58) Field of Classification Search
CPC . A61F 2/4425; A61F 2002/443; A61F 2/4455
See application file for complete search history.

(56) References Cited

U.S. PATENT DOCUMENTS

| | | | |
|---|---|---|---|
| 3,846,846 A | 11/1974 | Fischer | |
| 6,443,990 B1 | 9/2002 | Aebi et al. | |
| 7,854,766 B2 | 12/2010 | Moskowitz et al. | |
| 7,959,675 B2 | 6/2011 | Gately | |
| 8,241,364 B2 | 8/2012 | Hansell et al. | |
| 8,252,060 B2 | 8/2012 | Hansell et al. | |
| 8,506,629 B2 | 8/2013 | Weiland | |
| 8,529,628 B2 | 9/2013 | Marino et al. | |
| 8,641,764 B2 | 2/2014 | Gately | |
| 9,101,487 B2 | 8/2015 | Petersheim | |
| 9,198,772 B2 | 12/2015 | Weiman | |
| 9,204,972 B2 | 12/2015 | Weiman et al. | |
| 9,216,098 B2 | 12/2015 | Trudeau et al. | |
| 9,486,326 B2 | 11/2016 | Gahman et al. | |
| 9,492,286 B2 | 11/2016 | Biedermann et al. | |
| 9,554,918 B2 | 1/2017 | Weiman | |

(Continued)

FOREIGN PATENT DOCUMENTS

| | | |
|---|---|---|
| GB | 0 284 462 A | 2/1928 |
| WO | WO-2014/134590 A1 | 9/2014 |

OTHER PUBLICATIONS

International Search Report and Written Opinion in PCT/US2021/031596 dated Sep. 28, 2021 (12 pages).

*Primary Examiner* — Matthew J Lawson
(74) *Attorney, Agent, or Firm* — Foley & Lardner LLP

(57) ABSTRACT

A steerable expandable implant including a base member, an adjustable member coupled to the base member, the adjustable member movable between a collapsed position and an expanded position, a pivot member rotatably received by the base member and configured to receive a tool such that the tool and the pivot member are rotatable relative to the base member between a first position and a second position, wherein the pivot member is translationally fixed relative to the base member, and a first control member received by the base member, wherein manipulation of the first control member causes the adjustable member to move between the collapsed position and the expanded position.

16 Claims, 20 Drawing Sheets

(56) References Cited

U.S. PATENT DOCUMENTS

| | | |
|---|---|---|
| 9,622,879 B2 | 4/2017 | Taylor et al. |
| 9,770,343 B2 | 9/2017 | Weiman |
| 9,782,265 B2 | 10/2017 | Weiman et al. |
| 9,968,462 B2 | 5/2018 | Weiman |
| 10,004,607 B2 | 6/2018 | Weiman et al. |
| 10,064,742 B2 | 9/2018 | Taylor et al. |
| 10,470,894 B2 | 11/2019 | Foley et al. |
| 10,765,528 B2 | 9/2020 | Weiman et al. |
| 10,874,522 B2 | 12/2020 | Weiman |
| 10,874,523 B2 | 12/2020 | Weiman et al. |
| 2008/0140085 A1 | 6/2008 | Gately et al. |
| 2011/0166654 A1 | 7/2011 | Gately |
| 2011/0196494 A1 | 8/2011 | Yedlicka et al. |
| 2012/0010717 A1 | 1/2012 | Spann |
| 2012/0035730 A1 | 2/2012 | Spann |
| 2016/0051377 A1 | 2/2016 | Weiman et al. |
| 2017/0348116 A1 | 12/2017 | Weiman |
| 2018/0049885 A1 | 2/2018 | Weiman et al. |
| 2018/0243107 A1* | 8/2018 | Foley .................. A61F 2/4465 |
| 2018/0325693 A1 | 11/2018 | Weiman et al. |
| 2021/0015627 A1* | 1/2021 | Weiman ............... A61F 2/4425 |

\* cited by examiner

STEERABLE IMPLANT ASSEMBLY

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problems. With intravertebral devices, one or more spinal bodies are placed within a vertebra. Spinal devices, such as fusion cages and/or the like, are inserted into a spinal space either anteriorly, posteriorly, laterally or posteriolaterally.

SUMMARY

One embodiment relates to a steerable expandable implant including a base member, an adjustable member coupled to the base member, the adjustable member movable between a collapsed position and an expanded position, a pivot member rotatably received by the base member and configured to receive a tool such that the tool and the pivot member are rotatable relative to the base member between a first position and a second position, wherein the pivot member is translationally fixed relative to the base member, and a first control member received by the base member, wherein manipulation of the first control member causes the adjustable member to move between the collapsed position and the expanded position.

In some embodiments, the steerable expandable implant further includes a second control member coupled to the first control member, wherein the pivot member includes a bore extending therethrough and defining a first axis, wherein a second axis of the second control member is aligned with the first axis of the pivot member when the pivot member is in the first position. In some embodiments, the first axis of the pivot member at the second position is at an angle to the second axis of the second control member when the pivot member is in the second position. In some embodiments, the base member further includes an alignment portion configured to receive an alignment member of the tool to position the tool relative to the base member in the first and second positions, and wherein the base member includes an alignment protrusion configured to slidably engage an alignment track of the second control member and align the second control member to the base member. In some embodiments, an axis of the tool is parallel to an axis of the steerable expandable implant when the pivot member is in the first position. In some embodiments, a top surface of a first adjustable and a bottom surface of the base member define a height of the steerable expandable implant and are configured to engage adjacent portions of bone. In some embodiments, translation of the first control member changes a height of the steerable expandable implant. In some embodiments, a top surface of a first adjustable member and a bottom surface of a second adjustable member define a height of the steerable expandable implant and are configured to engage adjacent portions of bone, and wherein translation of the first control member changes a height of the steerable expandable implant.

Another embodiment relates to a steerable expandable implant including a base member, one or more adjustable members coupled to the base member, the adjustable member movable between a collapsed position and an expanded position, a first control member translationally coupled and pivotally fixed relative to the base member, and a second control member slidably coupled to the first control member and the adjustable member, wherein an axis of the second control member is offset relative to an axis of the first control member, wherein manipulation of the first control member causes at least one of the adjustable member to move between the collapsed position and the expanded position.

In some embodiments, the steerable expandable implant further comprises an adjustment member threadingly coupled to the first control member, wherein rotation of the adjustment member causes movement of the first control member. In some embodiments, the steerable expandable implant further comprises a pivot member pivotally received by the base member and configured to receive a tool such that the tool and the pivot member are pivotable relative to the base member. In some embodiments, the base member further includes an alignment portion configured to receive an alignment member of the tool to align the tool to the base member. In some embodiments, a top surface of a first adjustable member and one of a bottom surface of the base member or a bottom surface of a second adjustable member define a height of the steerable expandable implant. In some embodiments, the first control member includes a first guide extending into the base member and configured to limit a range of motion of the first control member, and wherein the second control member includes a second guide extending into the base member and configured to limit a range of motion of the second control member. In some embodiments, the second control member includes a control portion configured to slidably align the second control member with the base member.

Another embodiment relates to a method of positioning a spinal implant including coupling a tool to an implant, manipulating the tool to move the implant to a desired location, rotating the tool relative to a base member of the implant, coupling a control member of the tool to a first control member of the implant, and operating the control member of the tool to change a height of the implant.

In some embodiments, rotating the tool relative to the base member includes rotating the tool until the control member of the tool is axially aligned with the first control member. In some embodiments, operating the control member includes rotating the control member of the tool to cause translation of the first control member. In some embodiments, translation of the first control member causes translation of a second control member slidably coupled to an adjustable member of the implant. In some embodiments, the second control member includes at least one control portion slideably coupled to the adjustable member and configured to cause the adjustable member to move relative to the base member responsive to translation of the second control member.

BRIEF DESCRIPTION

The foregoing and other features of the present invention will become more apparent to one skilled in the art upon also reading the following description of embodiments with reference to the accompanying drawings.

Figure 1:
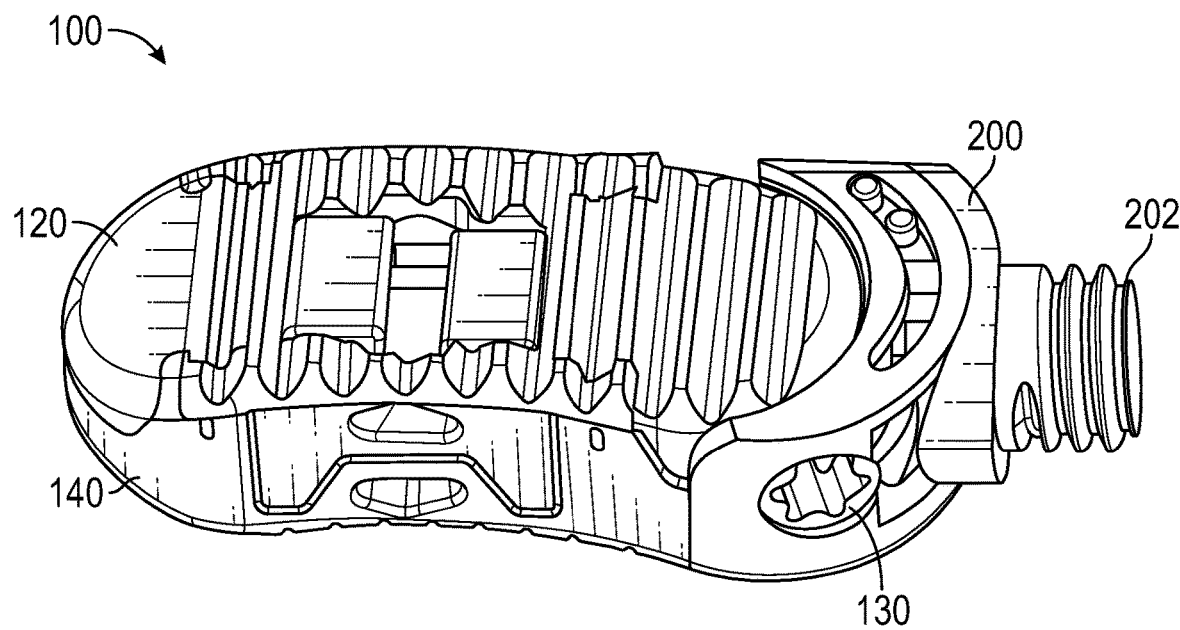
FIG. 1 is a perspective view of a steerable expandable implant in a first configuration, according to one embodiment.
Figure 2:
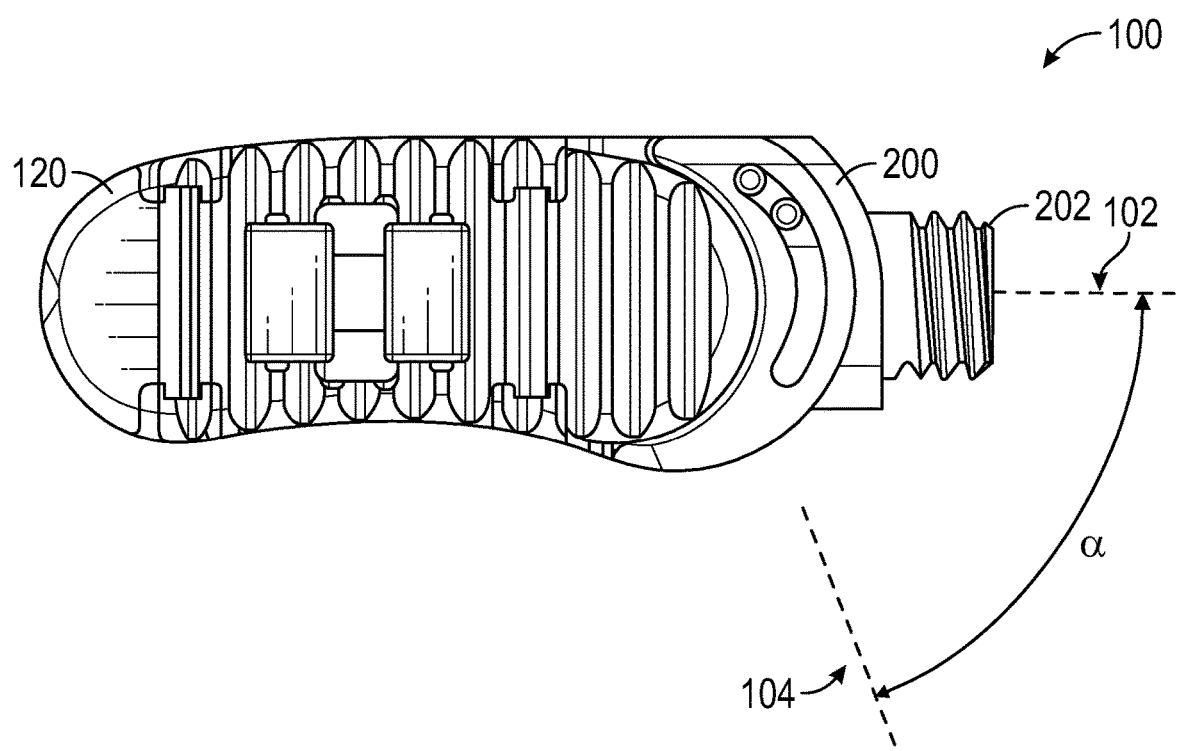
FIG. 2 is a top view of the steerable expandable implant of FIG. 1, according to one embodiment.
Figure 3:
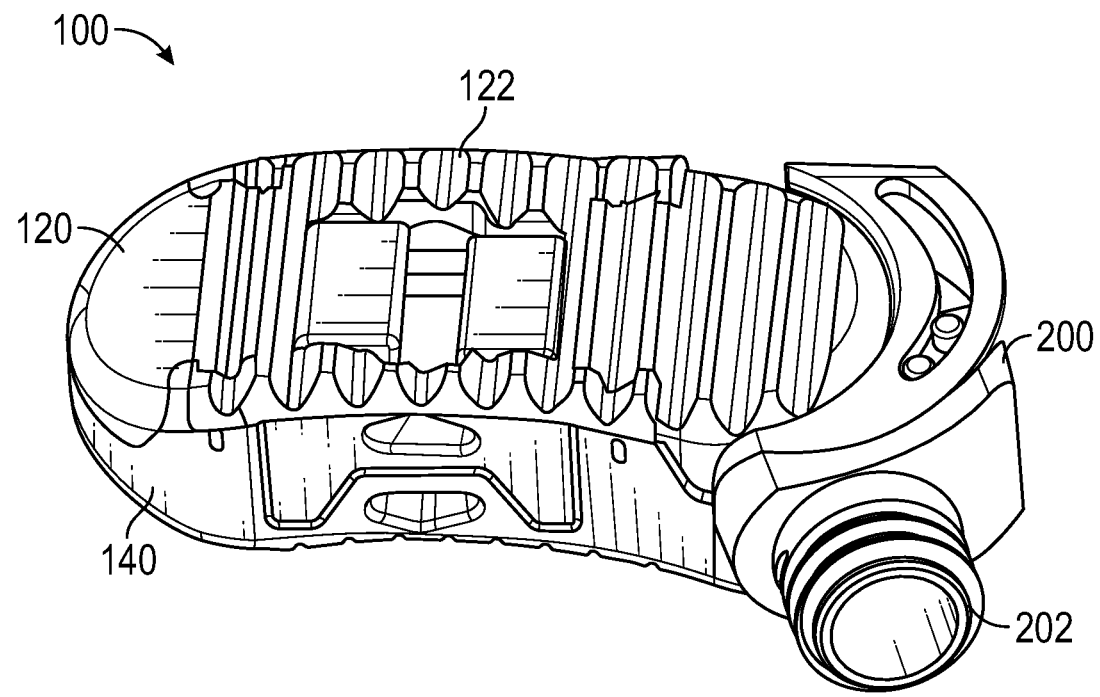
FIG. 3 is a perspective view of the steerable expandable implant of FIG. 1 in a second configuration, according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to steerable and expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (steerable and expandable/retractable) interbody/intravertebral body devices that are usable in a spinal column or other areas of a human.

Spinal interbody and intravertebral devices may be difficult to position. That is, a compact orientation, conducive to insertion, may be inconvenient to maneuver into a final position. Such spinal interbody and intravertebral devices lack the ability to change an orientation once inserted. This poses various problems with their use and/or implantation. Particularly, statically oriented spinal devices require complex positioning instruments or techniques to properly position the device and bridge the gap between adjacent vertebrae. These instruments and techniques do not lend themselves to microsurgery, arthroscopic surgery or the like.

Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing.

Various embodiments disclosed herein are directed to steerable expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to FIG. 1-7, steerable expandable implant 100 is shown, according to an exemplary embodiment. Implant 100 is usable, for example, between and/or within vertebral bodies of the spine, and may share many of the features of the other inter/intra-body implants discussed elsewhere herein. It should be understood that implant 100 may, in some embodiments, be usable in other portions of the body in addition to the spine, and all such applications are to be understood to be within the scope of the present disclosure.

Implant 100 may be inserted into a patient while in a first orientation. Once inserted, an appropriate tool may be used to engage a portion of the implant 100 to reorient the implant 100 into a second orientation. Implant 100 may be positioned within a desired space (e.g., between adjacent portions of bone) while in a first, collapsed position. An appropriate tool may be used to engage a portion of implant 100 to manipulate implant 100 into a desired position. Once in a desired position, the same or a subsequent tool may be utilized to engage a portion of implant 100 to expand implant 100 to a desired degree of expansion. It should be understood that based on a particular application, implant 100 may be utilized in a fully collapsed position, a fully expanded position, or any intermediate position therebetween. Once implant 100 is properly positioned and expanded to a desired height, bone graft material may be delivered by way of an access aperture and placed into a central cavity of implant 100. The various apertures in and through implant 100 may facilitate the growth of bone material in and around implant 100 to further stabilize implant 100.

Referring again to FIGS. 1-7, according to an exemplary embodiment, implant 100 includes base member 140 and adjustable member 120 adjustably coupled to the base member 140. In various embodiments, base member 140 includes alignment channels 144 and 146 to receive alignment portions 124 and 126. Alignment channels 144 and 146 and alignment portions 124 and 126 may align adjustable member 120 to base member 140. For example, the alignment features (e.g., alignment channels 144 and 146 and/or alignment portions 124 and 126) may facilitate alignment of adjustable member 120 to base member 140 during expansion of implant 100. The alignment features may couple to one another and allow for vertical (e.g., up and down, expansive and contractive, etc.) movement of base member 140 and adjustable member 120. In some embodiments, the alignment features have a relatively close fit to facilitate alignment between adjustable member 120 and base member 140, while in other embodiments, the alignment features have a relatively loose fit to facilitate a desired angular offset between adjustable member 120 and base member 140. In some embodiments, alignment channels 144 and 146 and alignment portions 124 and 126 form a tongue and groove joint. In various embodiments, alignment portions 124 and 126 include pin slots 125 and 127. Pin slots 125 and 127 may receive a pin inserted into apertures 143 to limit expansion and/or contraction of adjustable member 120. For example, pin slots 125 and 127 may facilitate expansion of adjustable member 120 such that adjustable member 120 cannot decouple from base member 140. Base member 140 and adjustable member 120 are shown to include surface patterns 122 and 148 respectively. Surface patterns 122 and 148 are configured to promote bonding to an adjacent surface (e.g., a portion of bone) and prevent slippage of implant 100. In some embodiments, surface patterns 122 and 148 are patterned ridges.

Implant 100 includes control member 200 coupled to an end of base member 140 and usable to manipulate implant 100 into a location on the patient. Control member 200 may rotate about the end of base member 140 between a first position 102 (shown in FIG. 2) and a second position 104 (shown in FIG. 4). First position 102 may reduce the cross-sectional footprint of implant 100 for implantation, allowing for smaller opening incisions and less invasive surgery techniques. Second position 104 may facilitate positioning implant 100 to align with the intended implantation location, thereby allowing for less reorientation of implant 100 and a more straightforward implantation. Control member 200 may include manipulation connector 202 to connect a tool for manipulation of implant 100 during implantation. In some embodiments, manipulation connector 202 is a male screw thread to receive a female mating thread. Implant 100 may include first control shaft 130 received by base member 140. First control shaft 130 may be used to expand implant 100. For example, a user may use a tool to manipulate (e.g., rotate, etc.) first control shaft 130 thereby causing expansion of implant 100. In various embodiments, an axis of first control shaft 130 aligns with an axis of control member 200 in the second position 104. Control member 200 may include an opening to facilitate access to first control shaft 130 while control member 200 is in the second position 104.

Figure 7:
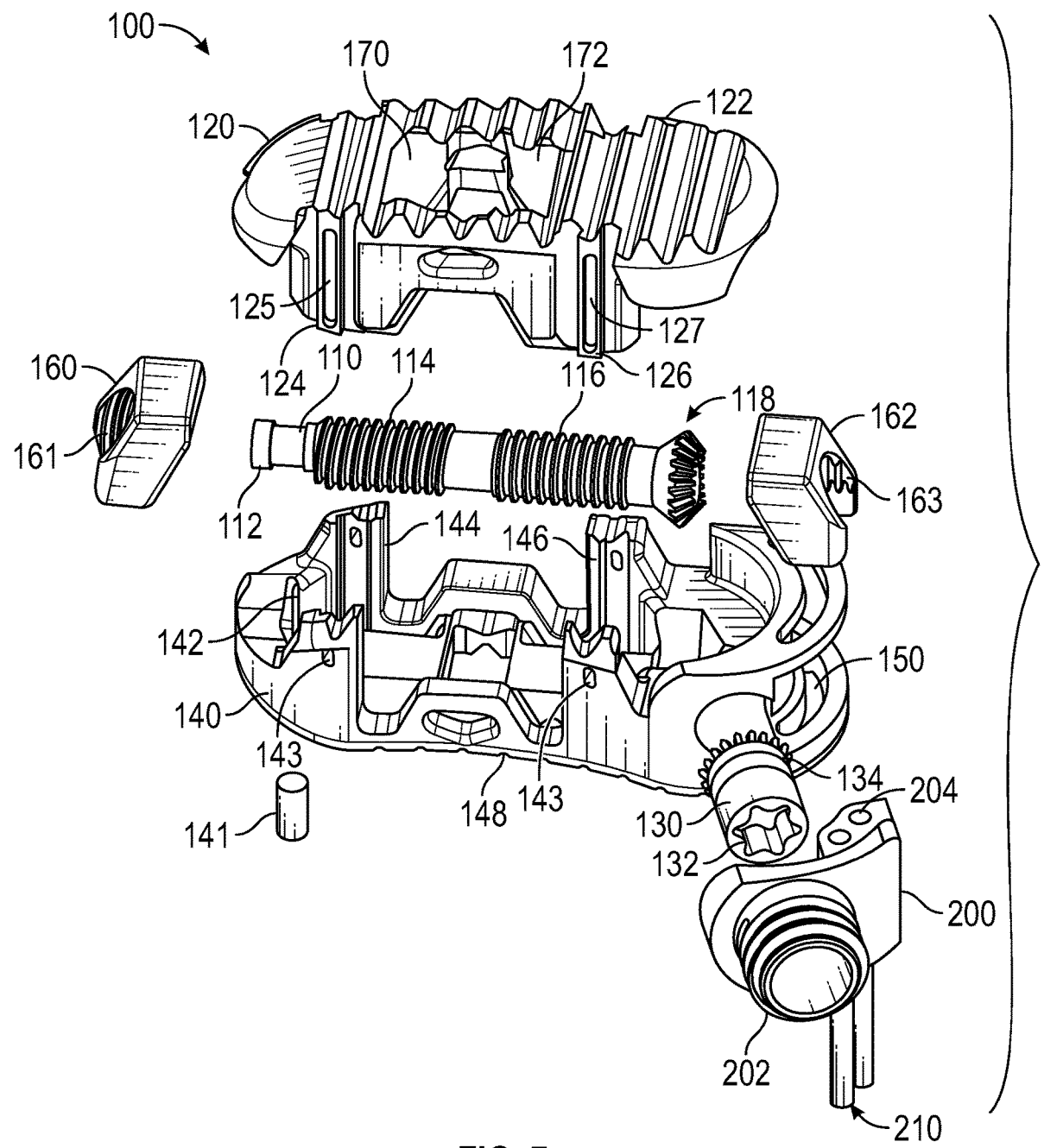
FIG. 7 is an exploded view of the steerable expandable implant of FIG. 1, according to one embodiment.
Figure 8:
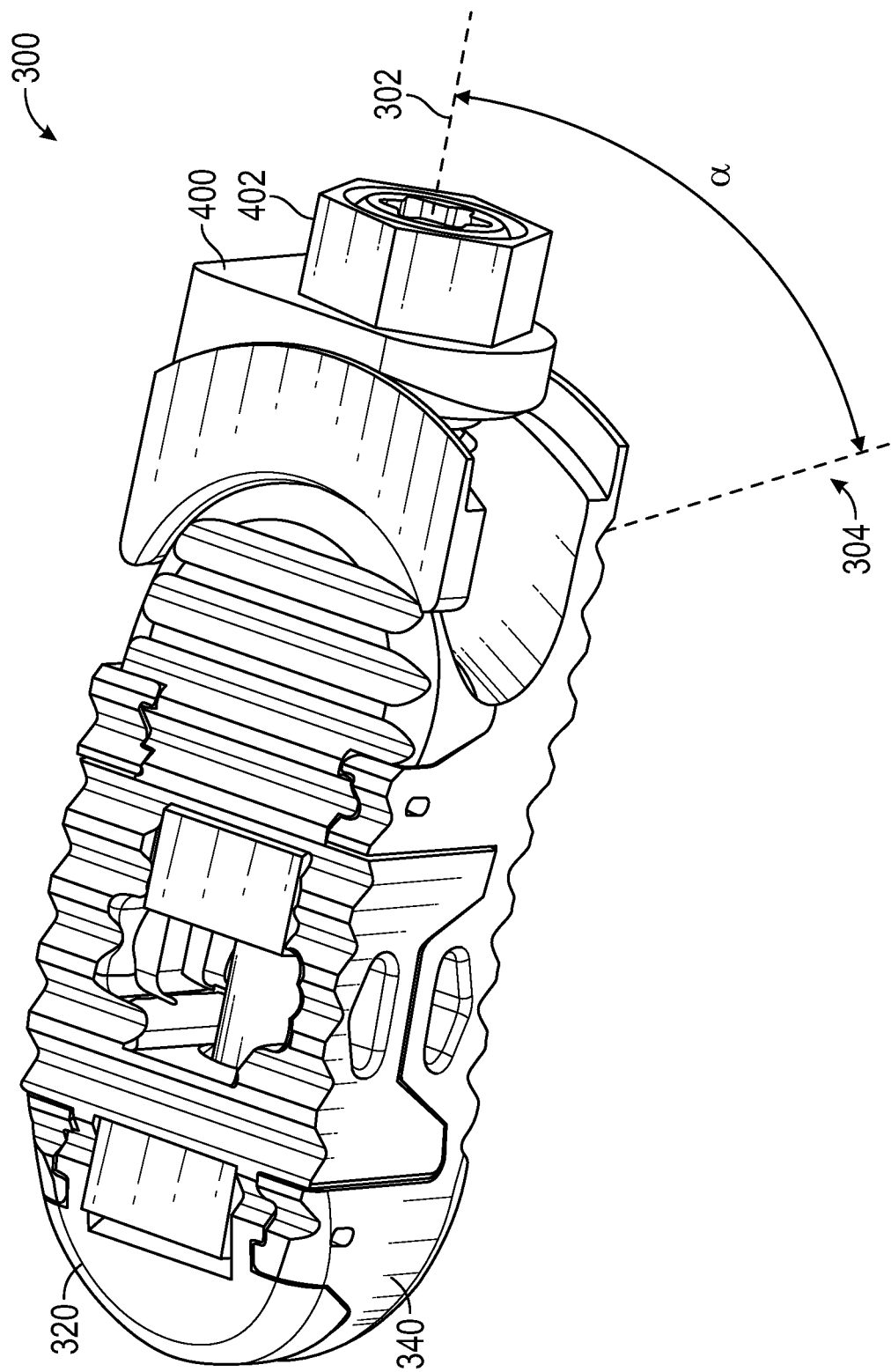
FIG. 8 is a perspective view of a steerable expandable implant in a first configuration, according to another embodiment.
Figure 9:
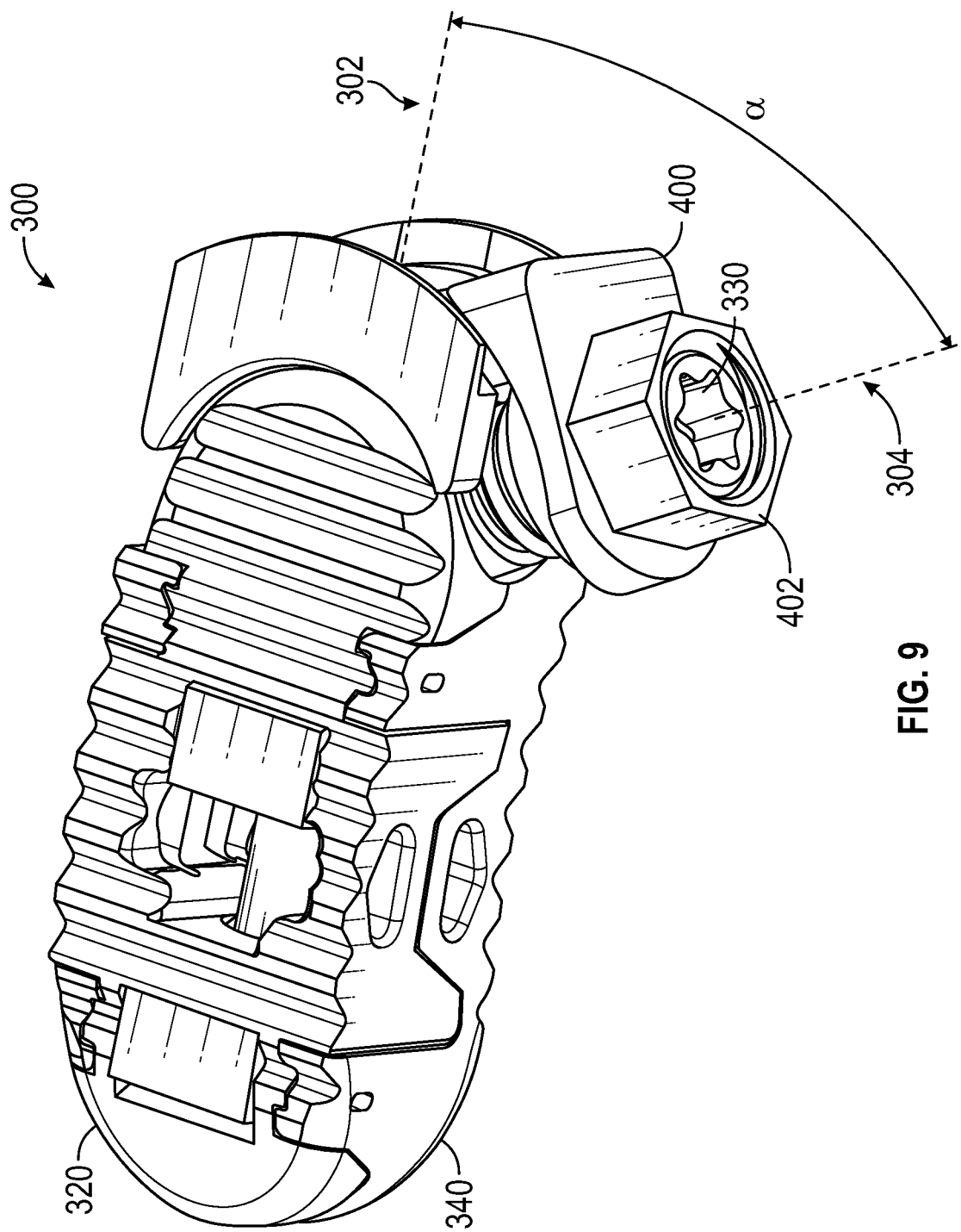
FIG. 9 is a perspective view of the steerable expandable implant of FIG. 8 in a second configuration, according to one embodiment.
Figure 10:
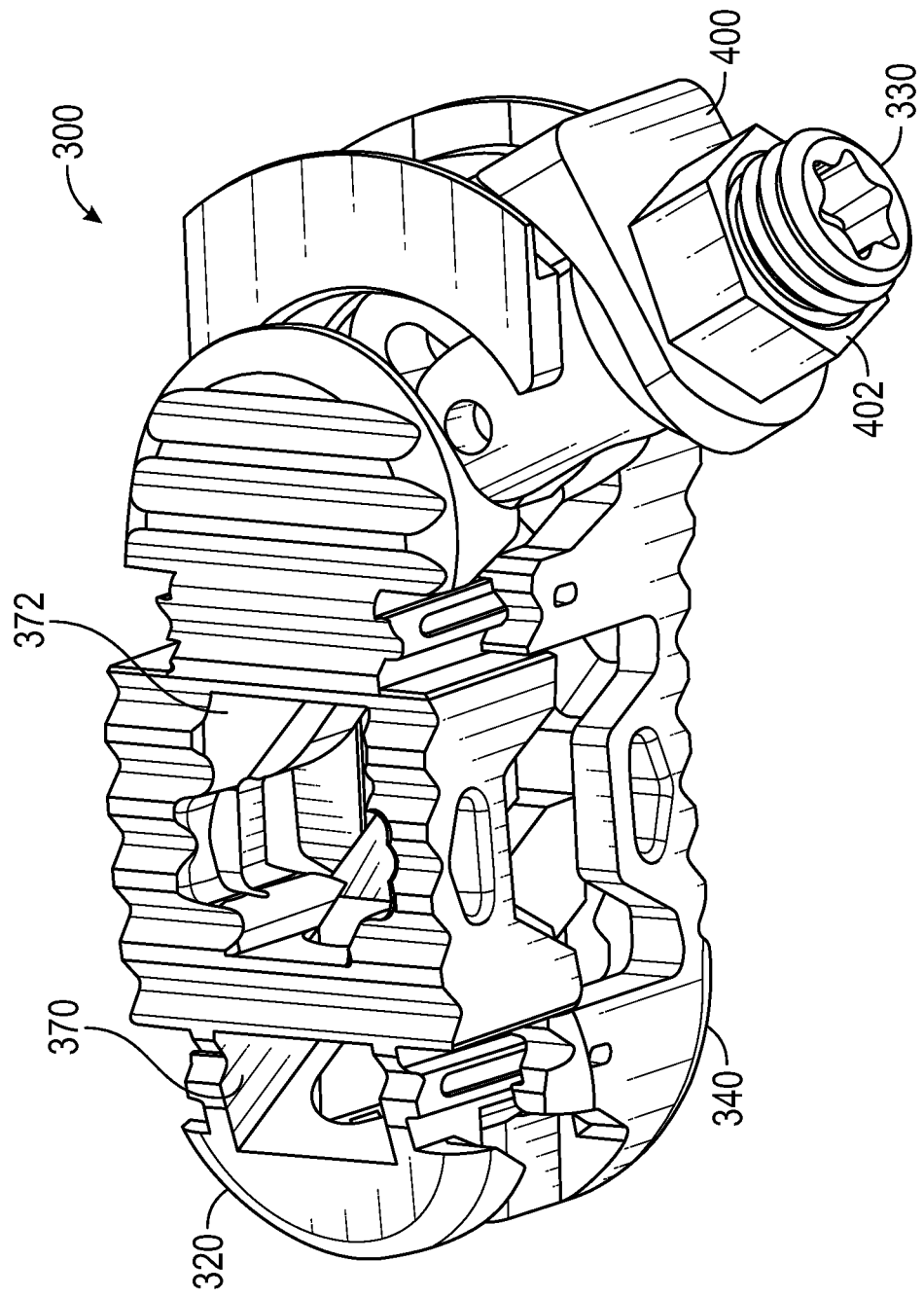
FIG. 10 is a perspective view of the steerable expandable implant of FIG. 8 in an expanded position, according to one embodiment.
Figure 11:
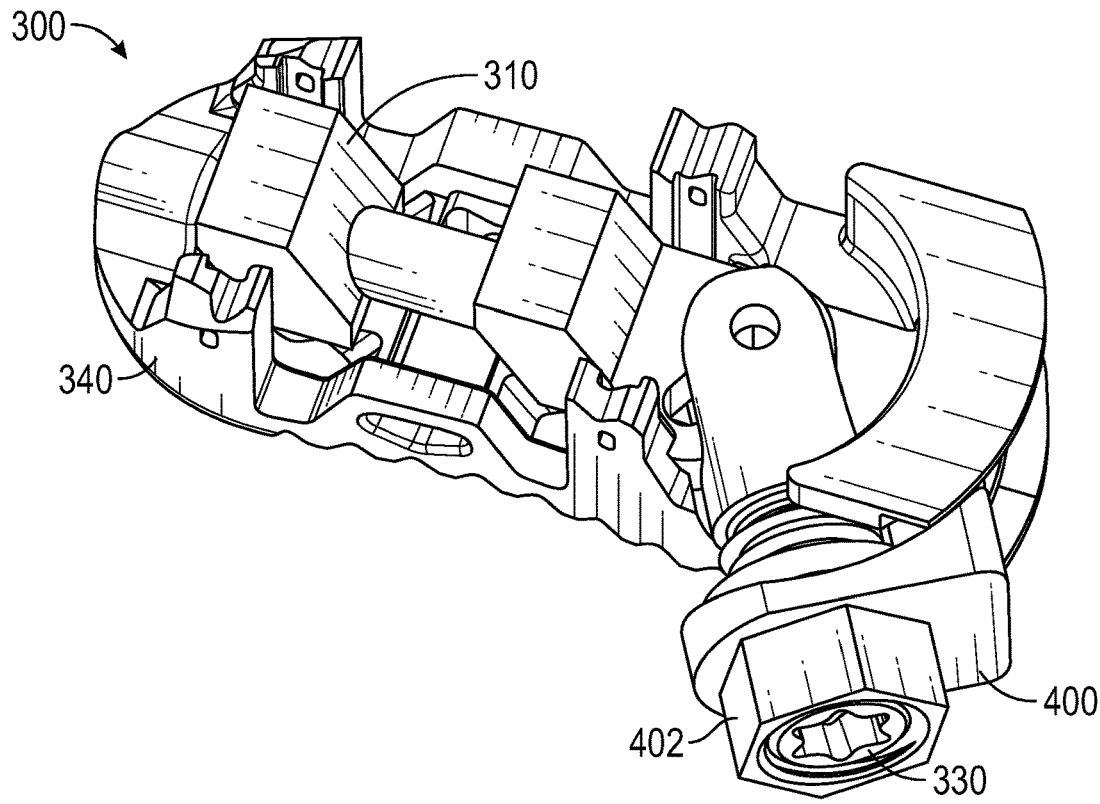
FIG. 11 is an internal view of a control shaft in a first position usable with the implants disclosed herein, according to one embodiment.
Figure 12:
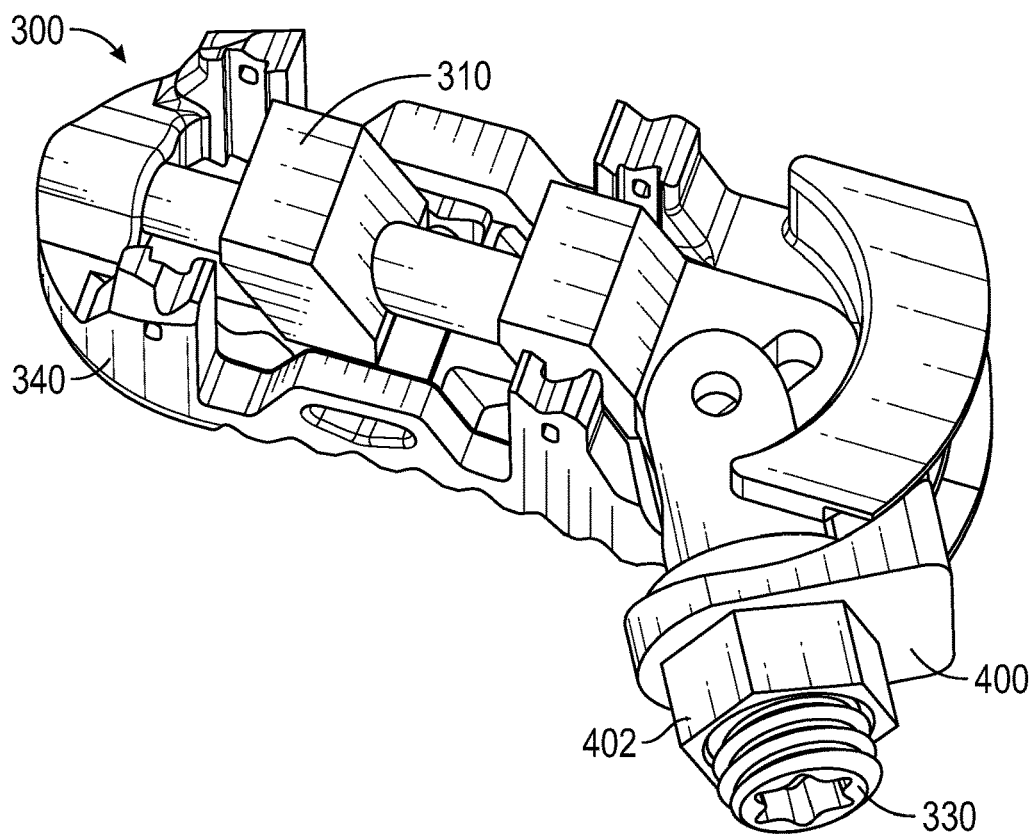
FIG. 12 is an internal view of a control shaft in a second position usable with the implants disclosed herein, according to one embodiment.

Referring now specifically to FIG. 7, first control shaft 130 may include or be coupled to connector 132 to receive a tool or other manipulation accessory. In some embodiments, connector 132 is a screw drive (e.g., Philips, Hex, Slot, etc.). In various embodiments, implant 100 includes a second control shaft 110 positioned between base member 140 and adjustable member 120. Second control shaft 110 may facilitate adjustment of the adjustable member 120 by transferring a force from a user to the adjustable member 120. In some embodiments, a user operates a different member (e.g., first control shaft 130) which transfers the operational force to second control shaft 110. First control shaft 130 may include engagement portion 134 configured to couple to contact 118 of second control shaft 110 and facilitate force transfer thereto. In some embodiments, engagement portion 134 is a geared portion to engage a corresponding geared portion of second control shaft 110. In various embodiments, second control shaft 110 and first control shaft 130 have different axes of rotation (i.e., are at an angle to one another). For example, first control shaft 130 may have a first axis that is conducive to manipulation by a user during implantation, while second control shaft 110 may have a second axis that facilitates adjustment of adjustable member 120. In some embodiments, second control shaft 110 includes one or more threaded portions 114 and 116. In some embodiments, implant 100 includes adjustment members 160 and 162 that may couple to second control shaft 110. Adjustment members 160 and 162 are shown to include threaded portions 161 and 163 respectively. Threaded portions 161 and 163 may correspond to the threaded portions 114 and 116 and couple thereto. Adjustment members 160 and 162 may translate along the axis of second control shaft 110. For example, rotation of second control shaft 110 may cause adjustment members 160 and 162 to move toward one another or away from one another. In some embodiments, threaded portion 114 and threaded portion 116 are threaded in opposite manners (e.g., left-handed and right-handed) such that, upon rotation of second control shaft 110, adjustment members 160 and 162 move in opposite directions along second control shaft 110. For example, second control shaft 110 may be configured such that rotation of second control shaft 110 in a first direction (e.g., clockwise) causes adjustment members 160 and 162 to move toward each other, and rotation of second control shaft 110 in a second direction (e.g., counter-clockwise) causes adjustment members 160 and 162 to move away from each other.

Second control shaft 110 is shown to include at one end connection 112 to be received by corresponding slot 142 in base member 140. Connection 112 may secure an end of second control shaft 110 and allow axial rotation of second control shaft 110. Pin 141 may be received within a vertical aperture of base member 140 and secure second control shaft 110. In various embodiments, pin 141 is received by a groove of second control shaft 110 thereby preventing horizontal translation of second control shaft 110.

Adjustable member 120 may include control channels 170 and 172 (see FIG. 7) to receive adjustment members 160 and 162 and cause an expansive or contractive translation based on movement of adjustment members 160 and 162. As adjustment members 160 and 162 translate along second control shaft 110, adjustable member 120 is moved upward or downward due to the angled shape of control channels 170 and 172. The rate of movement of adjustable member 120 can be adjusted by modifying the slope of control channels 170 and 172 relative to second control shaft 110. In some embodiments, the rate of movement of adjustable member 120 can be adjusted by modifying threaded portions 114 and 116 (e.g., lead, pitch, etc.) of second control shaft 110. Mechanisms of expandable implants are described in further detail in U.S. patent application Ser. No. 15/645,179 filed Jul. 10, 2017, the entirety of which is incorporated by reference herein.

Base member 140 may include guide channels 150. Guide channel 150 may receive pins 210 to couple control member 200 to base member 140. Pins 210 may be received by apertures 204 in control member 200 such that pins 210 extend beyond apertures 204 and are received in guide channels 150. Guide channels 150 may be configured to guide control member 200 in a path from the first position 102 (shown in FIG. 2) to the second position 104 (shown in FIG. 4). In some embodiments, control member 200, while in the second position 104, is configured to allow co-axial operation of first control shaft 130. For example, a tool attached to manipulation connector 202 may allow a user to operate first control shaft 130 to adjust adjustable member 120 while control member 200 is in the second position 104.

A non-limiting example of operation of control member 200 is as follows. A coaxial manipulation device may be attached to implant 100 via manipulation connector 202. Implant 100 may be inserted into the patient in the first position 102. In the first position 102, implant 100 is compact to allow for easy insertion. Once inside the patient, the user may move control member 200 from the first position 102 to the second position 104. In the second position 104, implant 100 is oriented to be aligned with an intended implant location on the patient, thereby reducing the amount of manual manipulation a user must perform to reorient implant 100 for alignment. Furthermore, in the second position 104, control member 200 is aligned with first control shaft 130 to facilitate operation of first control shaft 130 via the coaxial manipulation device. Once implant 100 is positioned in the intended location, the user may operate first control shaft 130, via the coaxial manipulation device, to adjust adjustable member 120 to a desired level of expansion to properly contact adjacent portions of bone.

Referring now to FIGS. 8-13, steerable expandable implant 300 is shown, according to an exemplary embodiment. Implant 300 may share many of the features of the other inter/intra-body implants discussed elsewhere herein. All such combinations of features are to be understood to be within the scope of the present disclosure. Implant 300 is generally similar to implant 100 in structure and function.

Implant 300 includes base member 340, adjustable member 320, and control member 400. Base member 340 and adjustable member 320 are configured to engage adjacent surfaces (e.g., portions of bone, etc.). In various embodiments, adjustable member 320 is coupled to base member 340 as described herein. Control member 400 is configured to facilitate manipulation of implant 300. For example, using a tool coupled to control member 400, a user may manipulate implant 300 into an implantation position. In various embodiments, base member 340, adjustable member 320, and/or control member 400 are the same or share features of base member 140, adjustable member 120, and/or control member 200.

In various embodiments, base member 340 includes alignment channels 344 and 346 to receive alignment portions 324 and 326. Alignment channels 344 and 346 and alignment portions 324 and 326 may align adjustable member 320 to base member 340. For example, the alignment features (e.g., alignment channels 344 and 346 and/or alignment portions 324 and 326) may facilitate alignment of adjustable member 320 to base member 340 during expansion of implant 300. The alignment features may couple to one another and allow for vertical (e.g., up and down, expansive and contractive, etc.) movement of base member 340 and adjustable member 320. In some embodiments, the alignment features have a relatively close fit to facilitate alignment between adjustable member 320 and base member 340, while in other embodiments, the alignment features have a relatively loose fit to facilitate a desired angular offset between adjustable member 320 and base member 340. In some embodiments, alignment channels 344 and 346 and alignment portions 324 and 326 form a tongue and groove joint. In various embodiments, alignment portions 324 and 326 include pin slots 325 and 327. Pin slots 325 and 327 may receive a pin inserted into apertures 343 to limit expansion and/or contraction of adjustable member 320. For example, pin slots 325 and 327 may facilitate expansion of adjustable member 320 such that adjustable member 320 cannot decouple from base member 340. Base member 340 and adjustable member 320 are shown to include surface patterns 322 and 348 respectively. Surface patterns 322 and 348 are configured to promote bonding to an adjacent surface (e.g., a portion of bone) and prevent slippage of implant 300. In some embodiments, surface patterns 322 and 348 are patterned ridges.

Implant 300 includes second control shaft 310 to affect an adjustment of adjustable member 320. Second control shaft 310 may be the same or share features of second control shaft 110. For example, second control shaft 310 may operate by a different principle than second control shaft 110. As a concrete example, second control shaft 310 may translate horizontally, while second control shaft 110 may rotate. Implant 300 includes first control shaft 330. First control shaft 330 may rotate about the end of base member 340 between a first position 302 (shown in FIG. 8) and a second position 304 (shown in FIG. 9).

Figure 13:
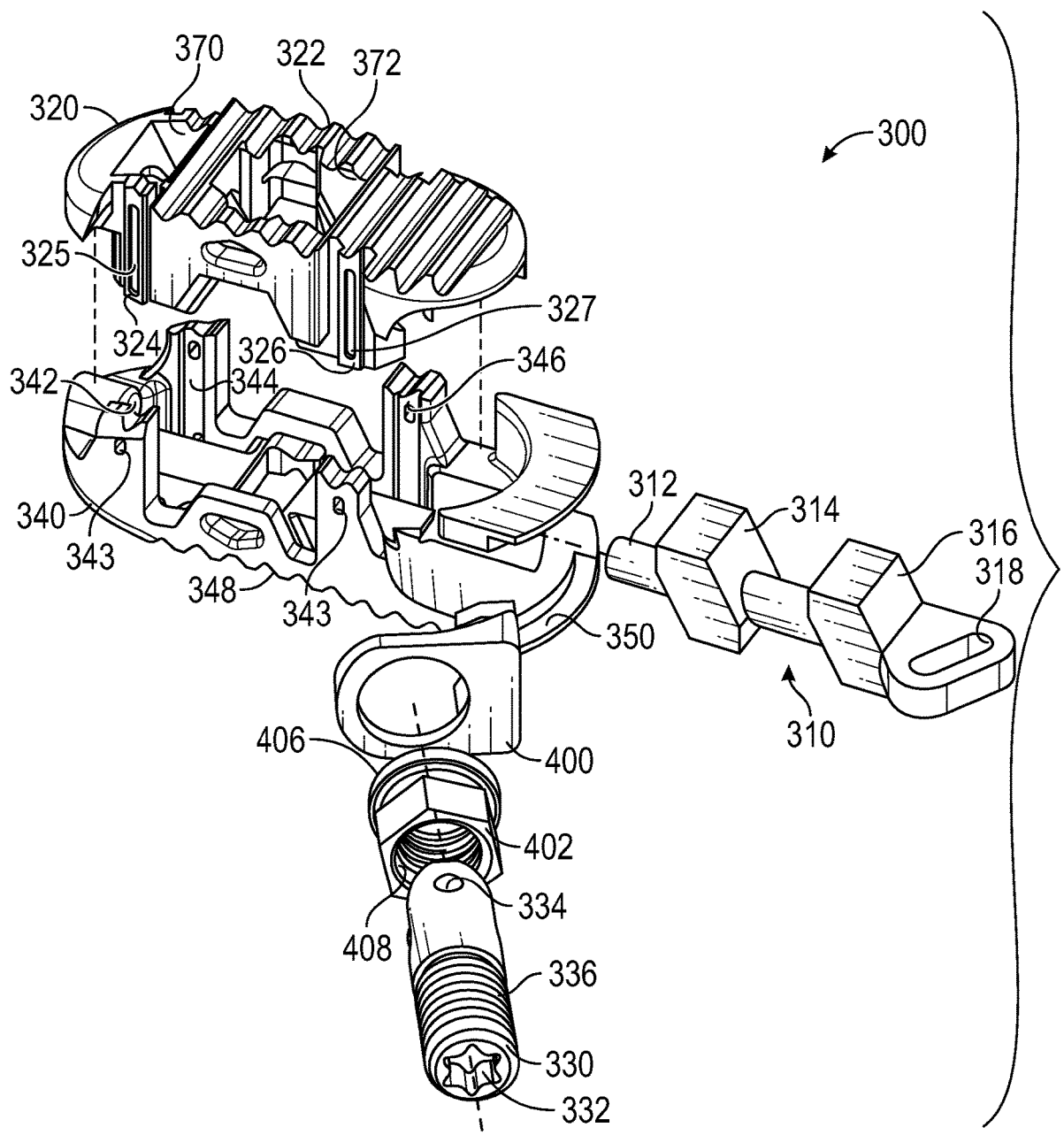
FIG. 13 is an exploded view of the steerable expandable implant of FIG. 8, according to one embodiment.

Referring now specifically to FIG. 13, first control shaft 330 may be received within control member 400 and manipulation connector 402. In various embodiments, first control shaft 330 includes engagement portion 336 to engage a corresponding engagement portion 408 of manipulation connector 402. In some embodiments, manipulation connector 402 is a nut and engagement portions 336 and 408 are screw threads. In some embodiments, a user may rotate manipulation connector 402 to affect a translation (e.g., inward or outward) of first control shaft 330. In some embodiments, first control shaft 330 includes connector 332 to facilitate translation of first control shaft 330. For example, a user may apply an axial force (e.g., inward or outward) to first control shaft 330 to facilitate rotation of manipulation connector 402 and/or translation of first control shaft 330. Connector 332 may be a screw drive (e.g., Philips, Hex, Slot, etc.).

Control member 400 may be configured to facilitate manipulation of implant 300 (e.g., to position implant 300 in an implantation location, etc.). In various embodiments, control member 400 may translate around an end of implant 300. In some embodiments, base member 340 includes guide channels 350 to facilitate translation of control member 400. In some embodiments, guide channels 350 are slotted grooves that receive alignment member 406 of manipulation connector 402. For example, alignment member 406 may be a protruded collar of manipulation connector 402 that rolls along guide channels 350. Additionally or alternatively, alignment member 406 may facilitate coupling manipulation connector 402 to control member 400. For example, alignment member 406 may include a groove that is received by control member 400 to rotatably couple manipulation connector 402 to control member 400. In some embodiments, rotation of manipulation connector 402, via the manipulation connector 402 or first control shaft 330, generates lateral movement across the end of implant 300 (e.g., along guide channels 350). For example, a user may rotate manipulation connector 402 counter-clockwise to move control member 400 between the first position 302 and the second position 304.

First control shaft 330 includes engagement portion 334 configured to facilitate coupling first control shaft 300 to second control shaft 310. In some embodiments, engagement portion 334 is an aperture to accept a link. For example, first control shaft 330 may connect to second control shaft 310 via a pin or other linking mechanism. Similarly, second control shaft 310 includes control channel 318 to receive a linking mechanism to link second control shaft 310 to first control shaft 330 and to guide translation (e.g., side to side) of second control shaft 310 in response to translation (e.g., inward or outward) of first control shaft 330.

Second control shaft 310 may include or be coupled to one or more interfaces 314 and 316 (e.g., control portions, etc.). In various embodiments, interfaces 314 and 316 are received within control channels 370 and 372 of adjustable member 320. As second control shaft 310 translates, adjustable member 320 is moved upward or downward due to the angled shape of control channels 370 and 372. The rate of movement of adjustable member 320 can be adjusted by modifying the slope of control channels 370 and 372 relative to second control shaft 310. Interfaces 314 and 316 may include angled portions that are configured to interface with control channels 370 and 372 to affect a vertical (e.g., up and down, expansive or contractive) movement of adjustable member 320 in response to a horizontal translation (e.g., side to side) of second control shaft 310. First control shaft 330 is configured to push or pull on second control shaft 310 via the linking mechanism between engagement portion 334 and control channel 318, thereby affecting a movement of adjustable member 320. Second control shaft 310 is shown to include contact 312 configured to couple to bore 342 of base member 340. Bore 342 may retain second control shaft 310 via contact 312 while allowing second control shaft 310 to slide (e.g., in and out of bore 342) freely.

A non-limiting example of operation of control member 400 is as follows. A coaxial manipulation device may be attached to implant 300 via manipulation connector 402. Implant 300 may be inserted into the patient in the first position 302. In the first position 302, implant 300 is compact to allow for easy insertion. Once inside the patient, the user may move control member 400 from the first position 302 to the second position 304. In the second position 304, implant 300 is oriented to be aligned with an intended implant location on the patient, thereby reducing the amount of manual manipulation a user must perform to reorient implant 300 for alignment. Once implant 300 is positioned in the intended location, the user may operate first control shaft 330, via the coaxial manipulation device, to adjust adjustable member 320 to a desired level of expansion to properly contact adjacent portions of bone.

Referring now to FIGS. 14-23, a steerable expandable implant 500 is shown according to an exemplary embodiment. Implant 500 may share many of the features of the other inter/intra-body implants discussed elsewhere herein. All such combinations of features are to be understood to be within the scope of the present disclosure. Implant 500 is generally similar to implant 300 in structure and function.

Referring now specifically to FIGS. 14-23, implant 500 includes base member 540 and adjustable member 520 adjustably coupled to base member 540. Base member 540 and adjustable member 520 are configured to engage adjacent surfaces (e.g., portions of bone, etc.). In various embodiments, adjustable member 520 is coupled to base member 540 as described herein. In various embodiments, base member 540 and/or adjustable member 520 are the same as or share features with base member 340 and/or adjustable member 320.

Figure 22:
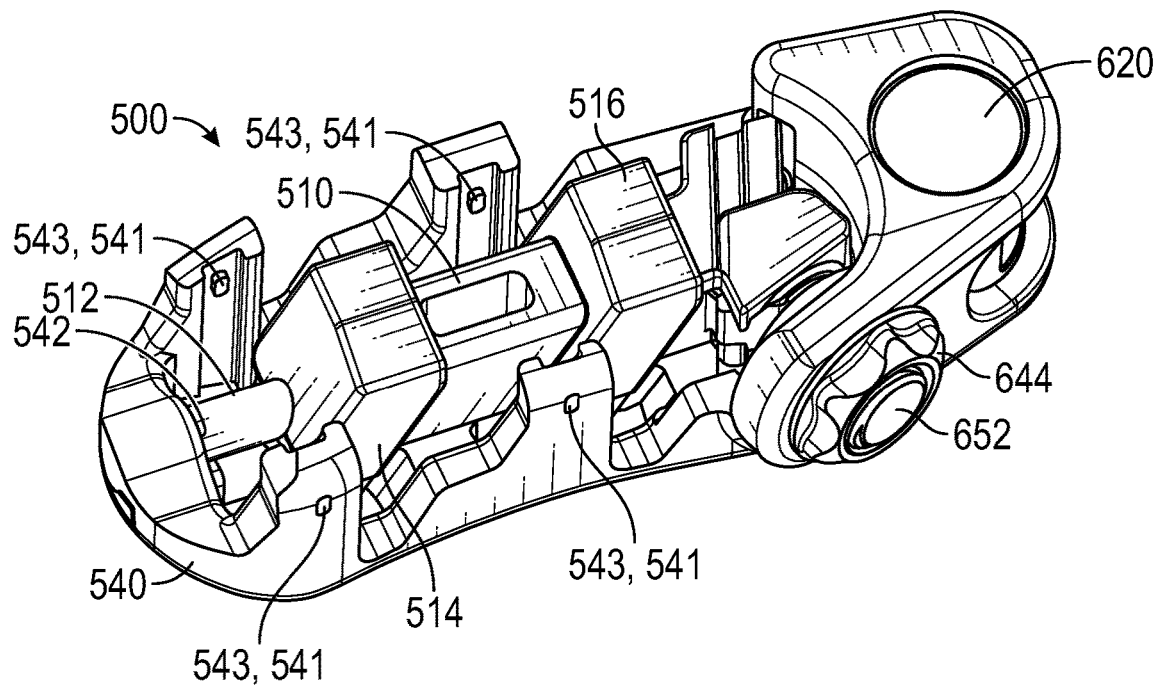
FIG. 22 is a perspective view of a control shaft in a first position usable with the implants disclosed herein, according to one embodiment.
Figure 23:
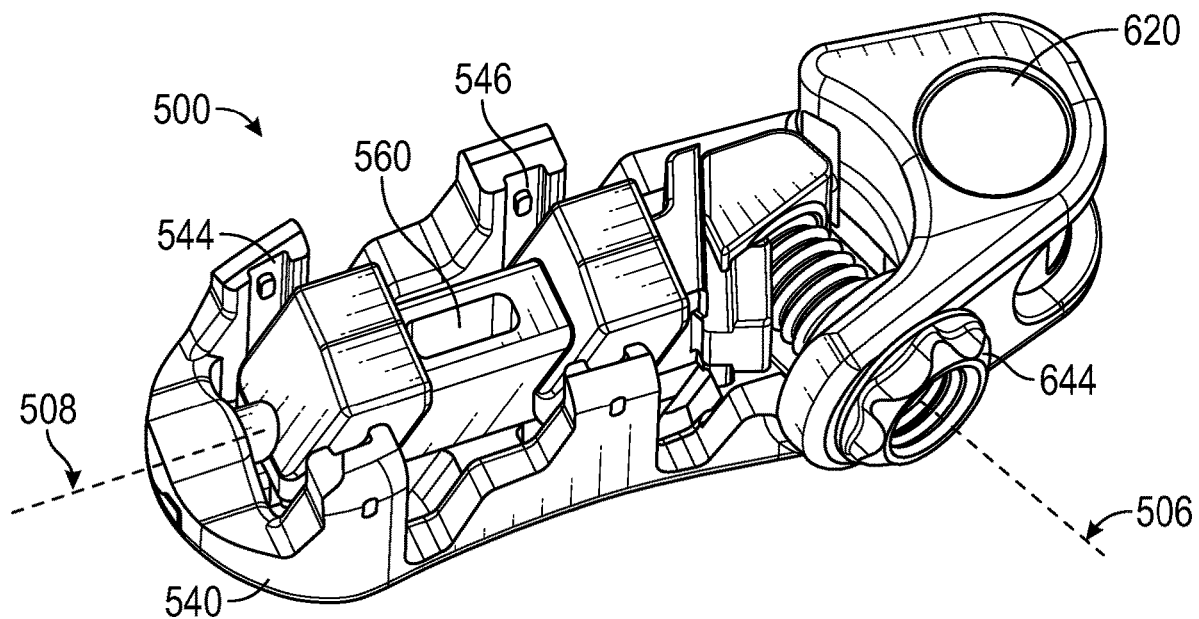
FIG. 23 is a perspective view of a control shaft in a second position usable with the implant disclosed herein, according to one embodiment.

In various embodiments, base member 540 includes alignment channels 544 and 546 to receive alignment portions 524 and 526. Alignment channels 544 and 546 and alignment portions 524 and 526 may align adjustable member 520 to base member 540. For example, the alignment features (e.g., alignment channels 544 and 546 and/or alignment portions 524 and 526) may facilitate alignment of adjustable member 520 to base member 540 during expansion of implant 500. The alignment features may couple to one another and allow for vertical (e.g., up and down, expansive and contractive, etc.) movement of base member 540 and adjustable member 520. In some embodiments, the alignment features have a relatively close fit to facilitate alignment between adjustable member 520 and base member 540, while in other embodiments, the alignment features have a relatively loose fit to facilitate a desired angular offset between adjustable member 520 and base member 540. In some embodiments, alignment channels 544 and 546 and alignment portions 524 and 526 form a tongue and groove joint. In various embodiments, alignment portions 524 and 526 include pin slots 525 and 527. As shown in FIG. 22, pin slots 525 and 527 may receive a pin 541 inserted into apertures 543 to limit expansion and/or contraction of adjustable member 520. For example, pin slots 525 and 527 may facilitate expansion of adjustable member 520 such that adjustable member 520 cannot decouple from base member 540. Base member 540 and adjustable member 520 are shown to include surface patterns 522 and 548 respectively. Surface patterns 522 and 548 are configured to promote bonding to an adjacent surface (e.g., a portion of bone) and prevent slippage of implant 500. In some embodiments, surface patterns 522 and 548 are patterned ridges.

Figure 15:
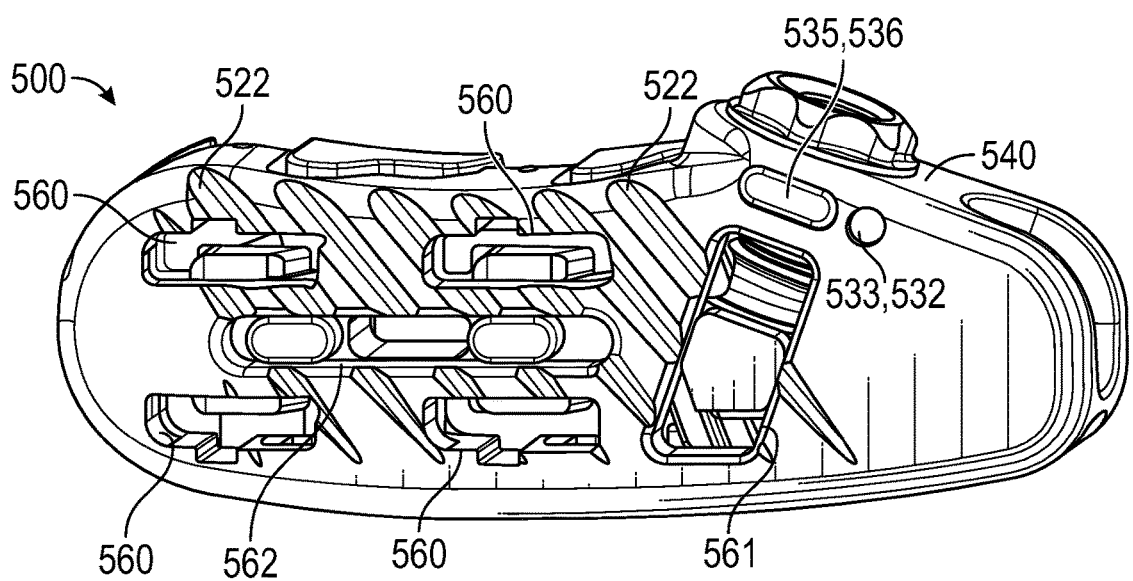
FIG. 15 is a bottom view of the steerable expandable implant of FIG. 15, according to one embodiment.

Implant 500 further includes second control member 510 (e.g., a control shaft, etc.). In various embodiments, second control member 510 translates along axis 508. In various embodiments, base member 540, adjustable member 520, and/or second control member 510 include apertures 560 (e.g., fluid apertures, bone growth material apertures, etc.), as shown in FIG. 15. Apertures 560 may facilitate fluid communication (e.g., for the delivery of bone growth material, etc.) between an exterior and an interior of implant 500. Second control member 510 includes control portions 514 and 516. Control portions 514 and 516 may include sloped portions of second control member 510 configured to contact corresponding sloped portions of adjustable member 520 and cause vertical translation or movement (e.g., up and down, expansive and contractive) of adjustable member 520 in response to horizontal (e.g., side to side) movement of second control member 510. In various embodiments, control portions 514 and 516 are received within control channels 570 and 572 of adjustable member 520. As second control member 510 translates, adjustable member 520 is moved upward or downward due to the angled shape of control channels 570 and 572. The rate of movement of adjustable member 520 can be adjusted by modifying the slope of control channels 570 and 572 relative to second control member 510. Control portions 514 and 516 may include angled portions that are configured to interface with control channels 570 and 572 to affect a vertical (e.g., up and down, expansive or contractive) movement of adjustable member 520 in response to a horizontal translation (e.g., side to side) of second control member 510. In various embodiments, second control member 510 includes guides 513 and 515 configured to direct horizontal translation of second control member 510 and/or limit a range of motion of second control member 510. In various embodiments, base member 540 may include track 562, as shown in FIG. 15. Track 562 may receive guides 513 and 515 and direct motion thereof. For example, track 562 may align second control member 510 to base member 540 throughout horizontal movement, as described above. Second control member 510 may further include end portion 512 configured to couple to bore 542 of base member 540. Bore 542 may retain second control member 510 via end portion 512 while allowing second control member 510 to slide (e.g., relative to bore 542) freely. In various embodiments, bore 542 is formed between bridge 530 and end 534. Bridge 530 may securely couple to end 534 thereby creating bore 542 to receive contact 512. In some embodiments, bridge 530 is permanently coupled to the base member 540 (e.g., via welding, etc.). Second control member 510 may include translation surface 518 configured to contact adjacent surface 656 of first control member 650 (e.g., an intermediate member, control member, etc.). First control member 650 may receive user input as described below and transfer the user input to second control member 510 by contacting translation surface 518. In various embodiments, surface 656 receives a horizontal force in a first direction from screw 652 and translates the horizontal force into a horizontal force in a second direction. For example, surface 656 may receive a first axial force along axis 506 and translate the force to cause axial motion of second control member 510 along axis 508. In various embodiments, surface 656 is coupled to first control member 650.

First control member 650 may be received within translation aperture 648 of base member 540. First control member 650 may include screw 652, guide 658 and surface 656. Screw 652 may include threaded portion 654 configured to contact a corresponding threaded portion of adjustment collar 640. In various embodiments, threaded portion 654 is a male screw thread to receive a female mating thread. Similar to guides 513 and 515, guide 658 is configured to direct horizontal translation of first control member 650 (e.g., limit a range of motion of first control member 650, etc.). In some embodiments, base member 540 includes track 561, as shown in FIG. 15. Track 561 may receive guide 658 and direct motion thereof. For example, track 561 may align first control member 650 within base member 540 throughout horizontal translation. In various embodiments, first control member 650 translates along axis 506. Additionally or alternatively, tracks 561 and 562 facilitate fluid communication similarly to apertures 560.

Adjustment collar 640 (e.g., an adjustment member, etc.) may be configured to be received within adjustment aperture 648 such that it contacts base member 540 and receives first control member 650. In some embodiments, base member 540 includes aperture 535 and 533 (e.g., as shown in FIG. 15). Aperture 535 and/or aperture 533 may receive a pin 532, 536 (e.g., linkage, collar, etc.) to couple adjustment collar 640 to base member 540. In some embodiments, the pin 532, 536 is received within a groove of adjustment collar 640. In various embodiments, adjustment collar 640 is rotatably received within adjustment aperture 648. Adjustment collar 640 includes collar 642, contact surface 644, and threaded aperture 646. Collar 642 may be a groove to maintain adjustment collar 640 within adjustment aperture 648. Contact surface 644 may be configured to receive a tool to facilitate user manipulation of implant 500. In various embodiments, contact surface 644 is a raised portion of adjustment collar 640 to facilitate transmission of an external rotational force to adjustment collar 640. Threaded aperture 646 may be configured to receive screw 652 of first control member 650 and translate force thereto. In various embodiments, threaded aperture 646 includes a female mating thread.

Figure 14:
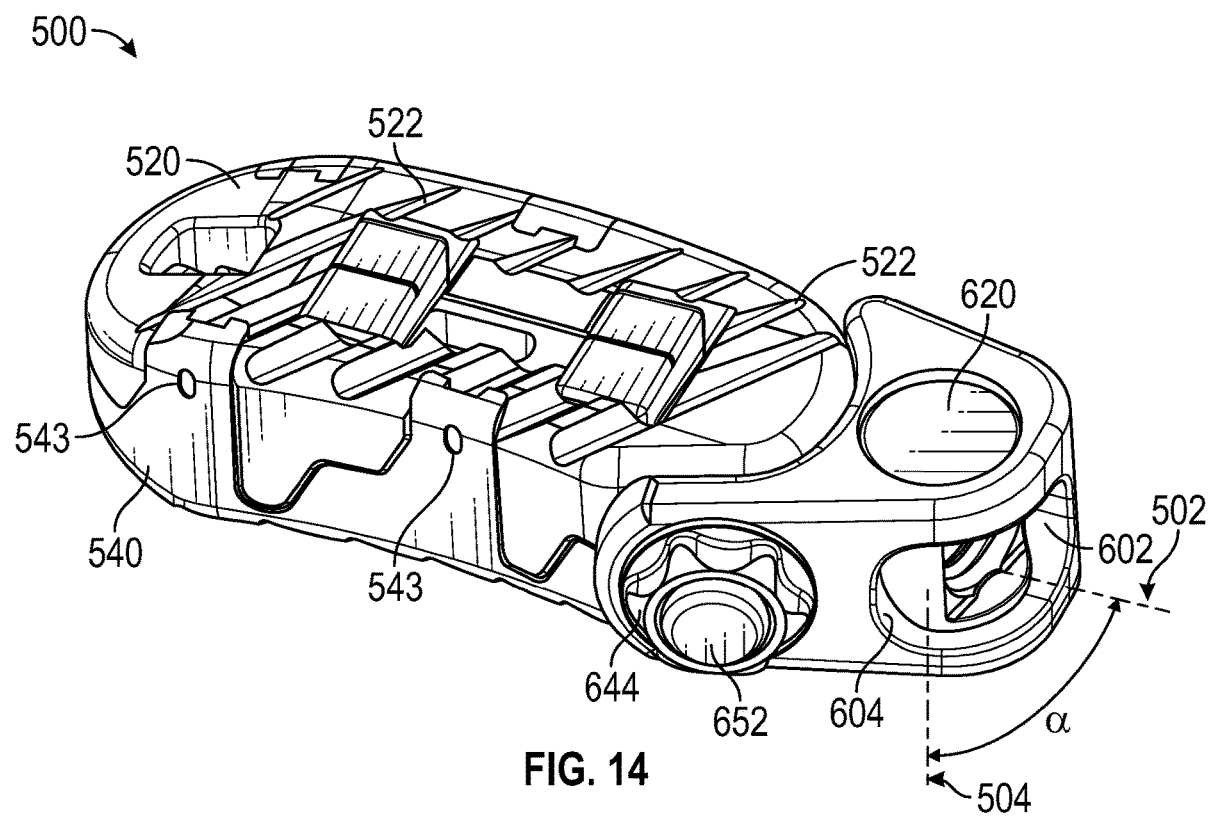
FIG. 14 is a perspective view of a steerable expandable implant, according to another embodiment.

Pivot member 620 may be received within aperture 624 of base member 540. In various embodiments, pivot member 620 is cylindrical. Pivot member 620 may rotate between a first position 502 and a second position 504, as shown in FIG. 14. In various embodiments, rotation of pivot member 620 is limited by limit 602 and/or limit 604. For example, limit 602 may prevent a user using a tool from rotating pivot member 620 farther counter-clockwise than the first position 502. In various embodiments, pivot member 620 may be rotatably received by aperture 626 such that pivot member 620 may rotate within aperture 626 but not decouple from base member 540. Pivot member 620 may include threaded aperture 622 configured to receive a corresponding threaded portion of a tool. In various embodiments, pivot member 620 facilitates positional adjustment of implant 500 as described in greater detail below.

Figure 16:
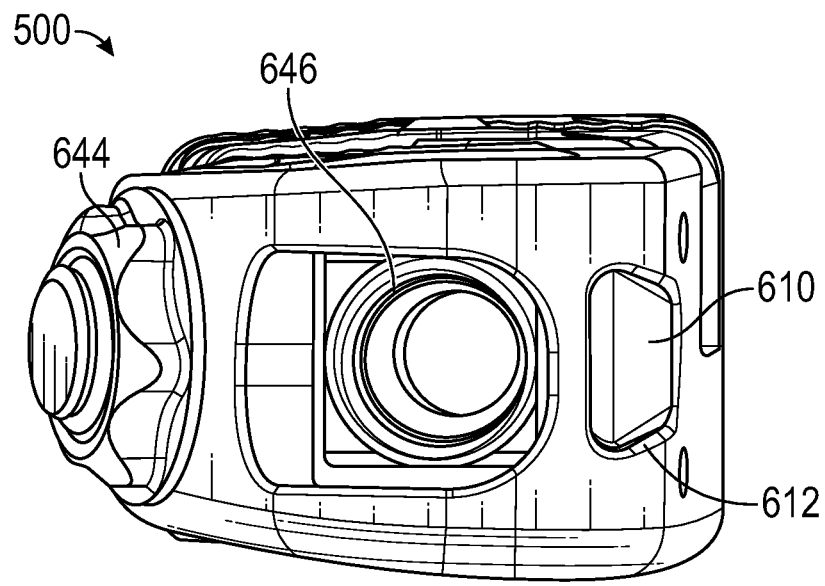
FIG. 16 is a right view of the steerable expandable implant of FIG. 15, according to one embodiment.
Figure 17:
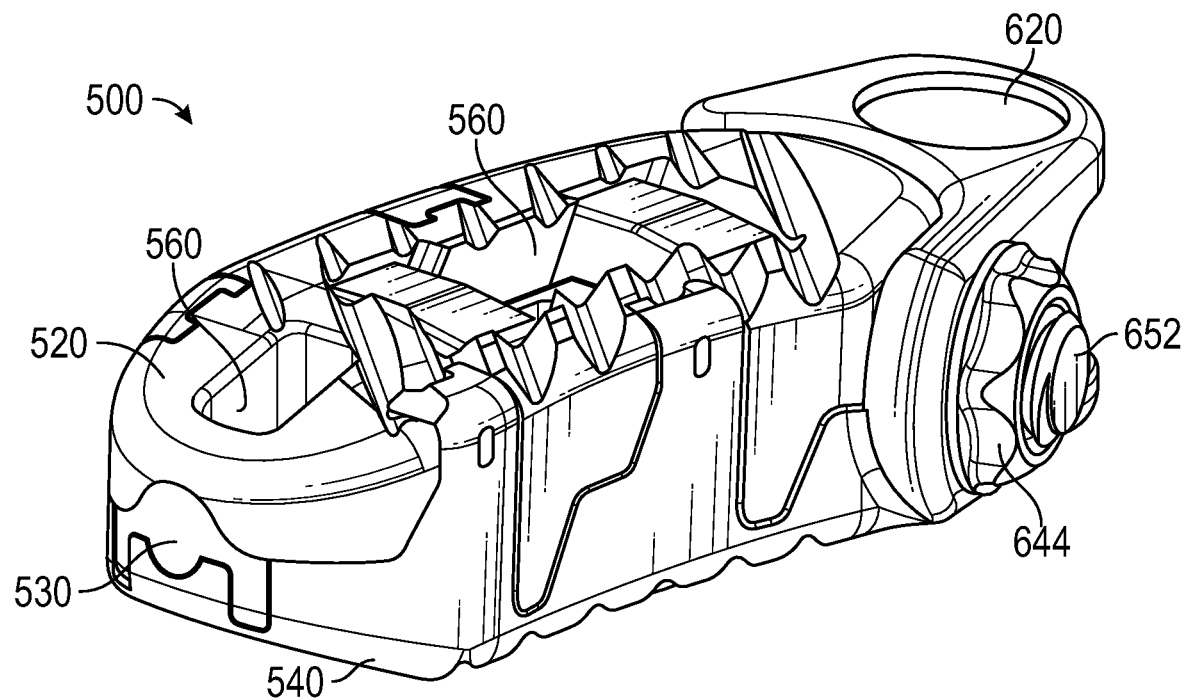
FIG. 17 is a left perspective view of the steerable expandable implant of FIG. 15, according to one embodiment.
Figure 18:
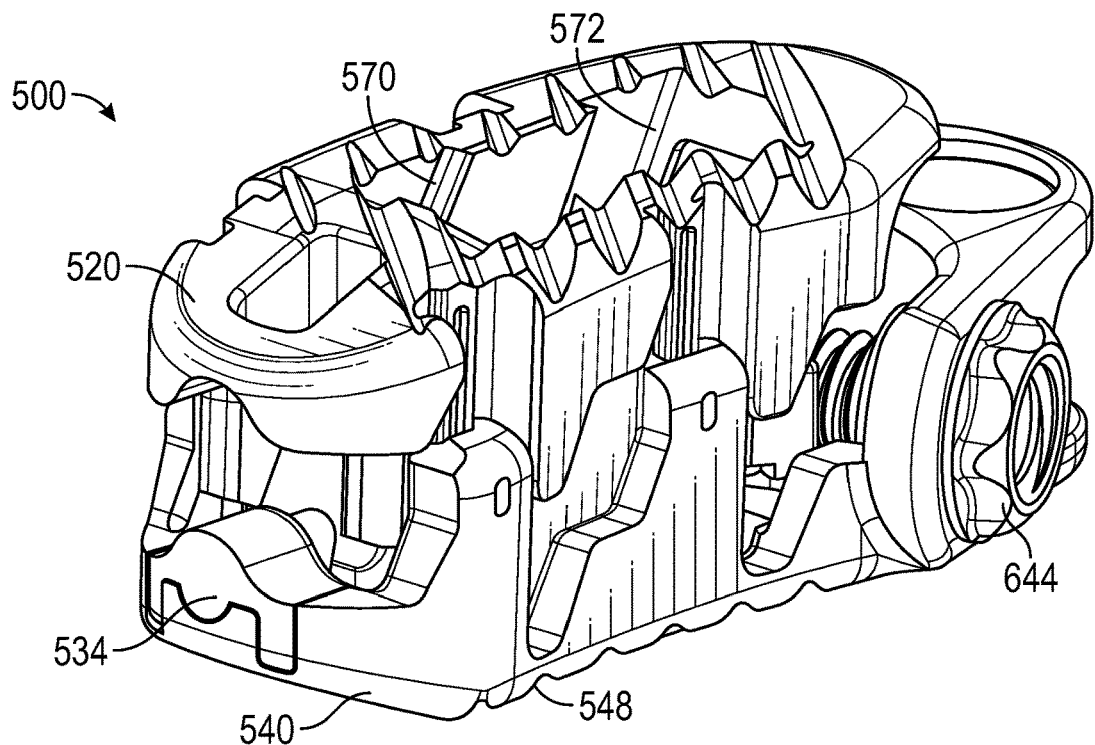
FIG. 18 is a left perspective view of the steerable expandable implant of FIG. 15 in an expanded position, according to one embodiment.
Figure 19:
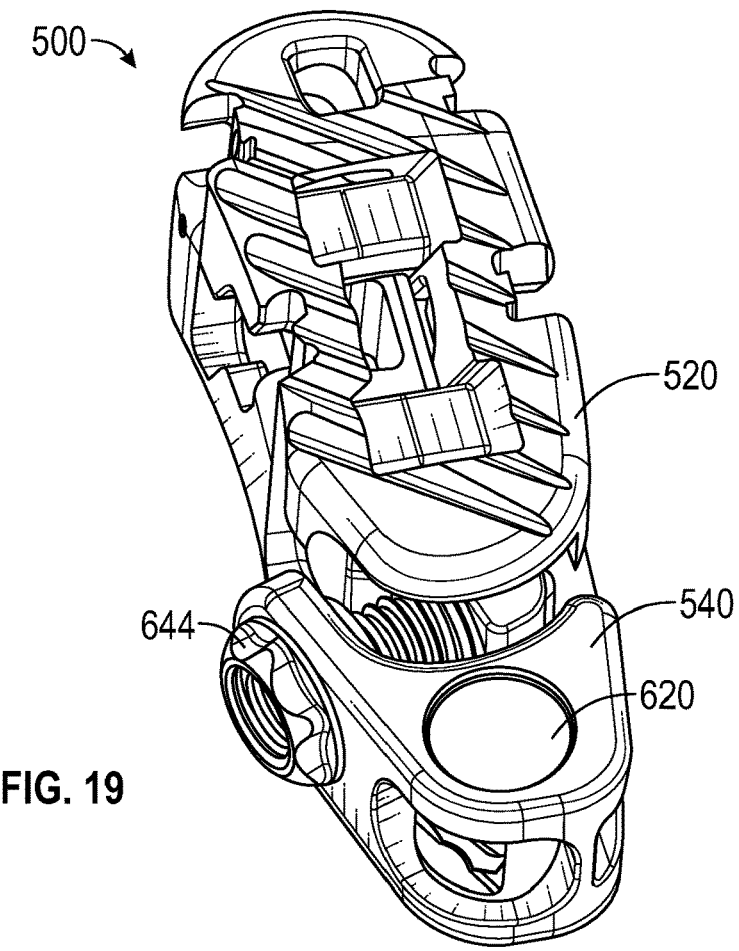
FIG. 19 is a right perspective view of the steerable expandable implant of FIG. 15 in the expanded position, according to one embodiment.
Figure 20:
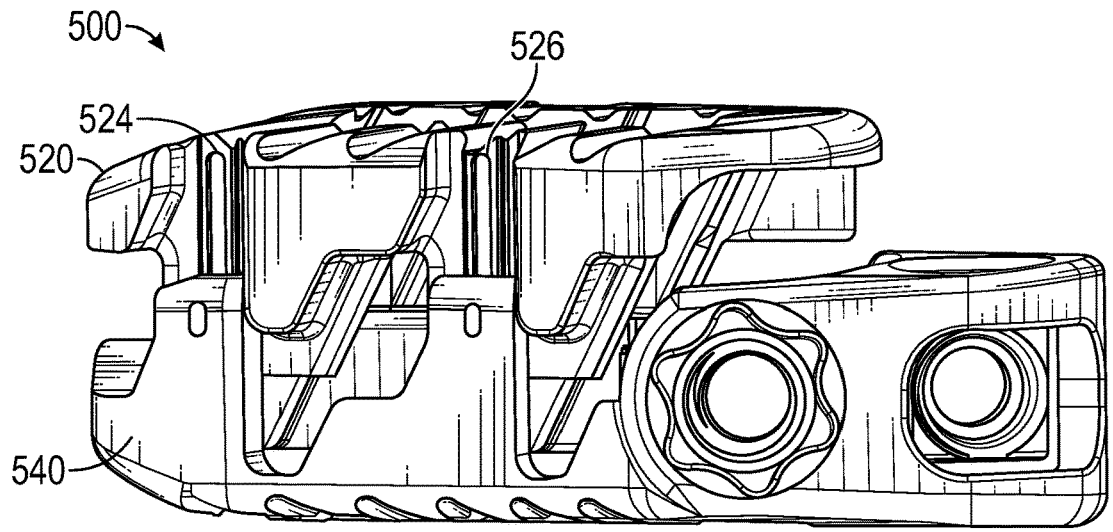
FIG. 20 is a front view of the steerable expandable implant of FIG. 15 in the expanded position, according to one embodiment.
Figure 21:
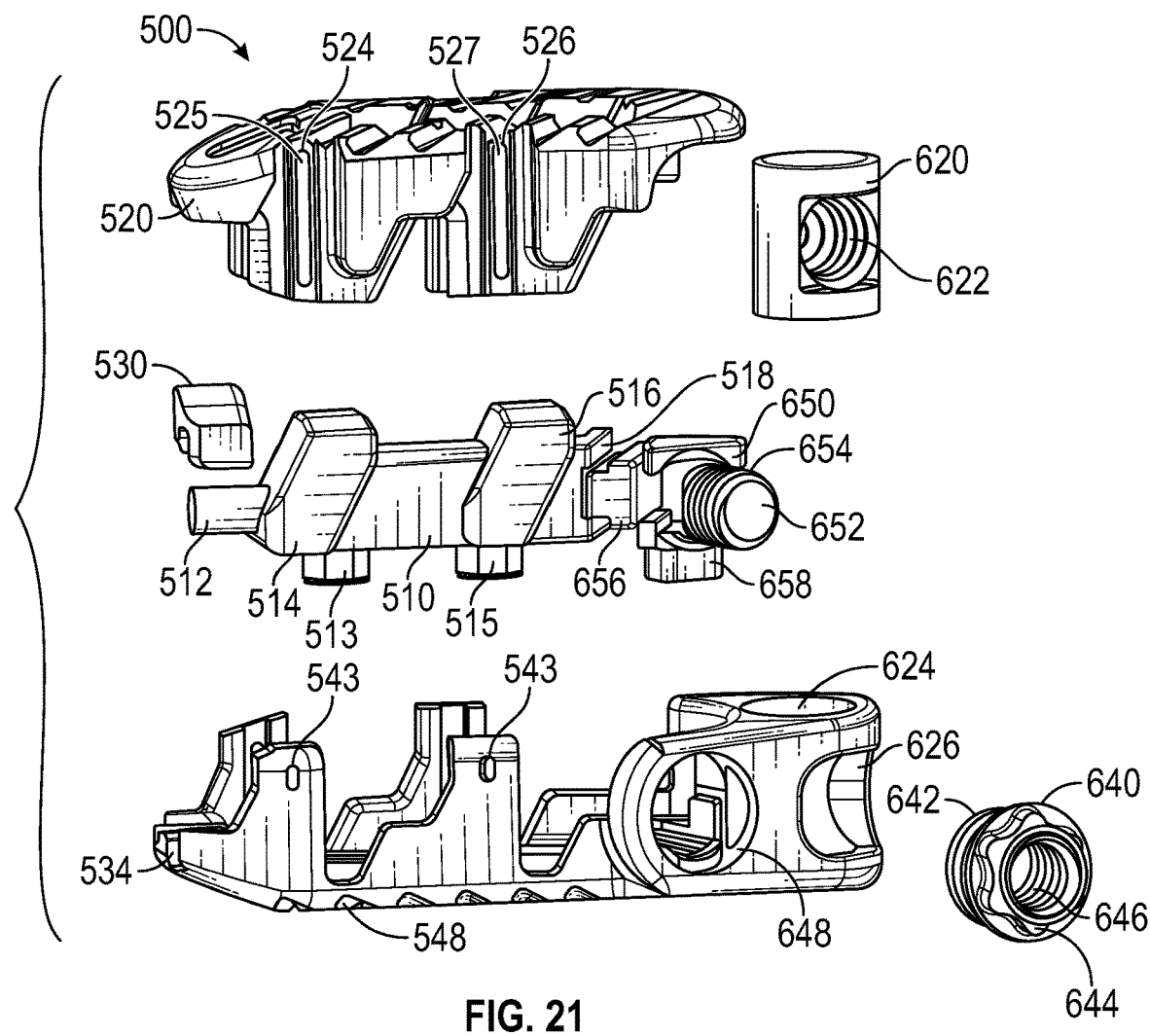
FIG. 21 is an exploded view of the steerable expandable implant of FIG. 15, according to one embodiment.

Base member 540 further includes tool recess 610, as shown in FIG. 16. Tool recess 610 may be configured to receive a tool to facilitate manipulation of implant 500 by a user. In various embodiments, tool recess 610 includes slanted side walls 612 to facilitate coupling to a tool. Tool recess 610 is discussed in greater detail below with reference to FIGS. 27-34.

A non-limiting example of operation of implant 500 is as follows. A tool, such as a coaxial manipulation device, may be attached to implant 500 via pivot member 620. A user may align the manipulation device to implant 500 using tool recess 610. The user may turn pivot member 620 from the first position 502 to the second position 504 within aperture 624, while changing an orientation of implant 500. In the second position 504, the user may engage adjustment collar 640 using the manipulation device. Rotation of adjustment collar 640 causes translation of first control member 650 (e.g., along axis 506). First control member 650 engages of second control member 510, causing translation or other movement of second control member 510 (e.g., along axis 508). Translation of second control member 510 causes control portions 514 and 516 to engage control channels 570 and 572, thereby causing expansion or contraction of adjustable member 520. In various embodiments, first control member 650 and second control member 510 are coupled (e.g., via a tongue and groove joint, a dovetail interface, etc.). Rotation of adjustment collar 640 in a first direction may cause expansion of implant 500 and rotation of adjustment collar 640 in a second direction may cause contraction of implant 500 (e.g., first control member 650 pulls second control member 510, thereby causing movement of adjustable member 520).

Figure 24:
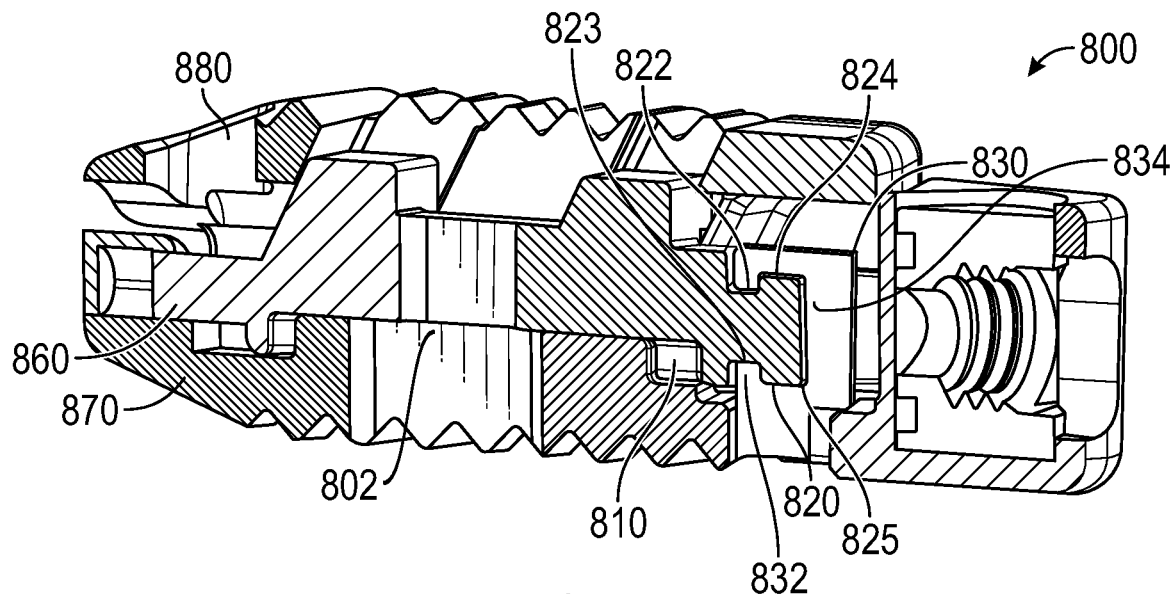
FIG. 24 is a cutaway view of a steerable expandable implant, according to another embodiment.
Figure 25:
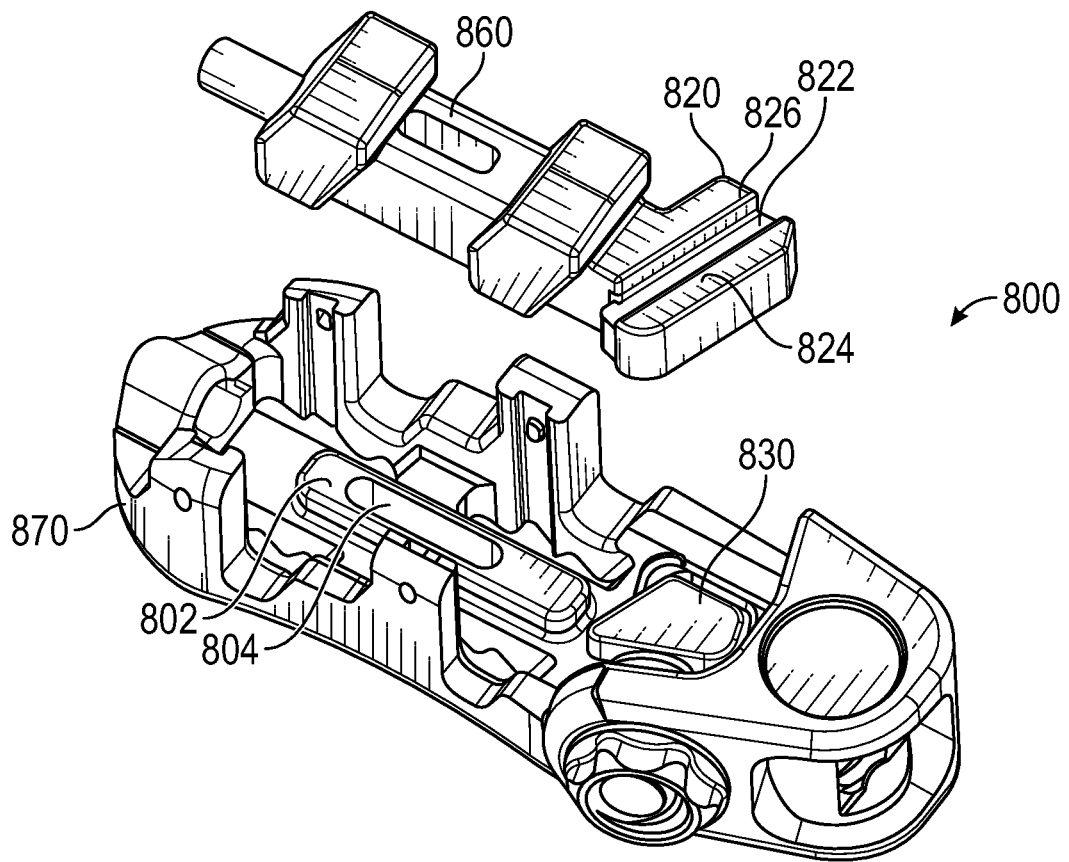
FIG. 25 is an exploded view of the steerable expandable implant of FIG. 24, according to one embodiment.
Figure 26:
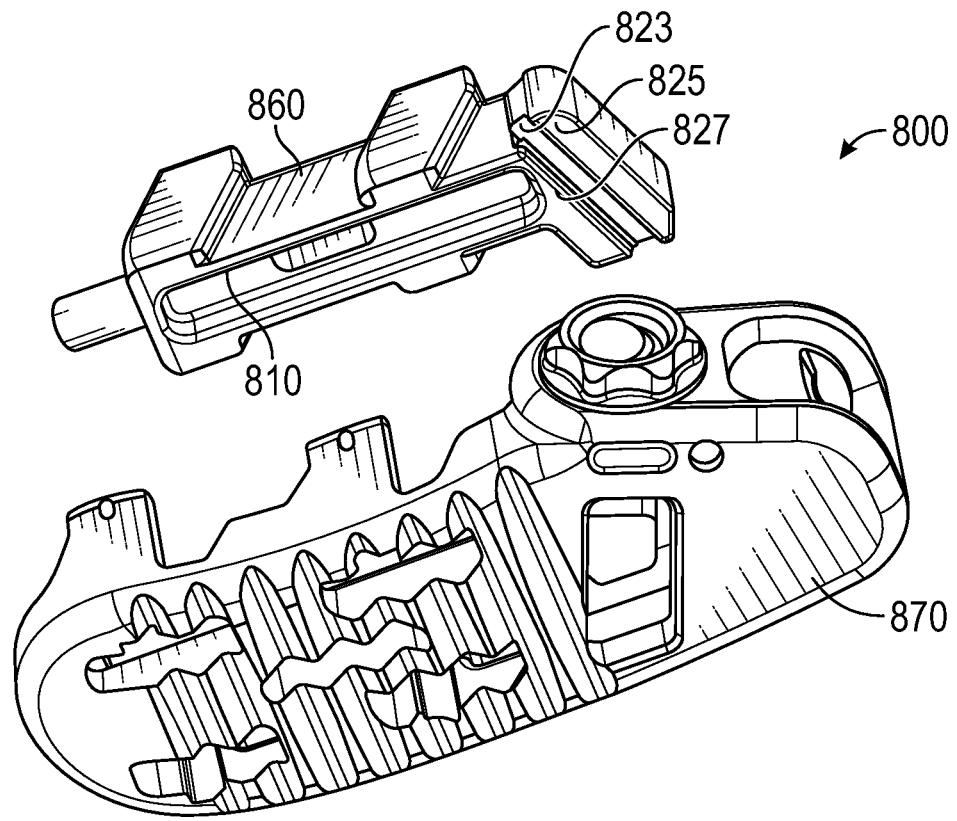
FIG. 26 is another exploded view of the steerable expandable implant of FIG. 24, according to one embodiment.

Referring now to FIGS. 24-26, a steerable expandable implant 800 is shown, according to an exemplary embodiment. Implant 800 may share many of the features of the other inter/intra-body implants discussed elsewhere herein. All such combinations of features are to be understood to be within the scope of the present disclosure. Implant 500 is generally similar to implant 300 and implant 500 in structure and function.

Implant 800 may include base member 870 and adjustable member 880 adjustably coupled to base member 880. Base member 870 and adjustable member 880 are configured to engage adjacent surfaces (e.g., portions of bone, etc.). In various embodiments, base member 870 and/or adjustable member 880 are the same as or share features with base member 540 and/or adjustable member 520.

Base member 870 may include protrusion 802 configured to interface with pocket 810 in second control member 860. Protrusion 802 may facilitate alignment of second control member 860 during translation of second control member 860. For example, protrusion 802 may fit inside of pocket 810 (e.g., alignment channel, etc.) and align second control member 860 with base member 870 during side to side translation of second control member 860. In various embodiments, protrusion 802 is configured to be a track that second control member 860 slides along. In various embodiments, second control member 860 includes pocket 810. Pocket 810 may be a negative space within second control member 860 configured to receive protrusion 802. In various embodiments, protrusion 802 includes aperture 804 (e.g., fluid apertures, bone growth material apertures, etc.), as shown in FIG. 25. Aperture 804 may facilitate fluid communication (e.g., for the delivery of bone growth material, etc.) between an exterior and an interior of implant 800.

Implant 800 further includes second control member 860 (e.g., a control shaft, etc.). Second control member 860 may share many of the features of second control member 510. In various embodiments, second control member 860 includes first control portion 820 configured to interface with first control member 830 (e.g., as shown in FIG. 24). In various embodiments, first control portion 820 and first control member 830 interface using a tongue and groove joint. In various embodiments, first control portion 820 includes first surface 826 and/or second surface 827. First surface 826 and/or second surface 827 may be a portion of first control portion 820 at a first height. In various embodiments, first surface 826 is on a top of first control portion 820 and second surface 827 is on a bottom of first control portion 820. In various embodiments, first control portion 820 includes top channel 822 and bottom channel 823. In various embodiments, top channel 822 and/or bottom channel 823 form a groove to receive a portion of first control member 830 to facilitate coupling first control member 830 to second control member 860. In various embodiments, a surface of top channel 822 and/or bottom channel 823 is at a different height than that of first surface 826 and/or second surface 827 (e.g., a surface of top channel 822 may be below a surface of first surface 826, etc.). First control portion 820 may include third surface 824 and fourth surface 825. In various embodiments, third surface 824 is on a top portion of first control portion 820 and fourth surface 825 is on a bottom portion of first control portion 820. First surface 826, second surface 827, third surface 824, and fourth surface 825 may form top channel 822 and/or bottom channel 823. In some embodiments, a height of third surface 824 is different than a height of first surface 826 (e.g., lower than, etc.). Additionally or alternatively, a height of fourth surface 825 may be different than a height of second surface 827.

In various embodiments, first control member 830 includes groove 834 configured to receive first control portion 820. In various embodiments, first control member 830 includes retention portion 832. Retention portion 832 may be a lip configured to interface with top channel 822 and/or bottom channel 823. In various embodiments, a top portion of groove 834 includes retention portion 832. Additionally or alternatively, a bottom portion of groove 834 may include retention portion 832. In various embodiments, groove 834 and retention portion 832 are configured to couple first control member 830 to second control member 860 while facilitating translation of second control member 860. For example, first control surface 820 may slide within groove 834 to translate movement of first control member 830 in a first direction to movement of second control member 860 in a second direction. In various embodiments, an axis of groove 834 and an axis of top channel 822 and/or bottom channel 823 are aligned. In various embodiments, first control portion 820 slideably engages first control member 830. In various embodiments, first control member 830 is the same or similar to first control member 650. For example, first control member 830 may be first control member 650 but including pocket 810.

Figure 27:
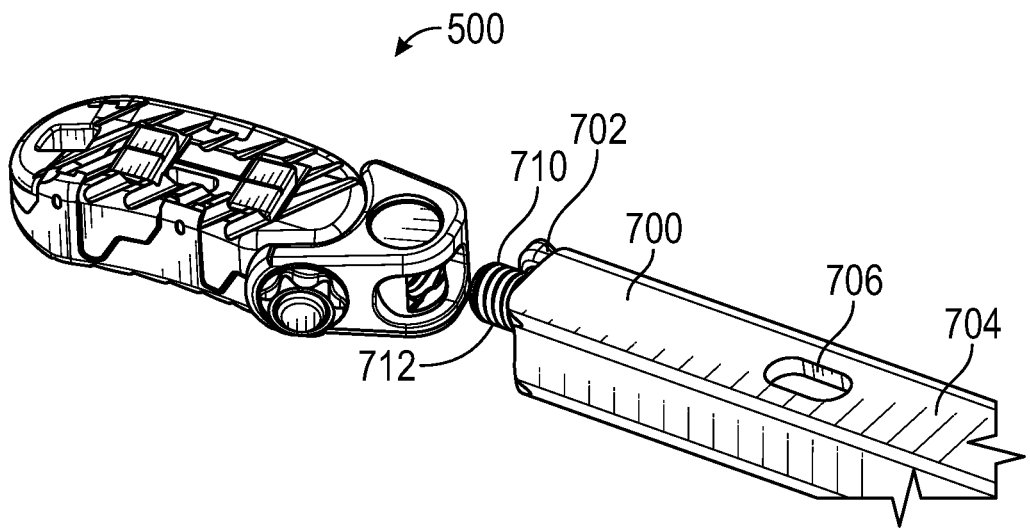
FIG. 27 is a perspective view of a tool for positioning an implant, according to one embodiment.
Figure 28:
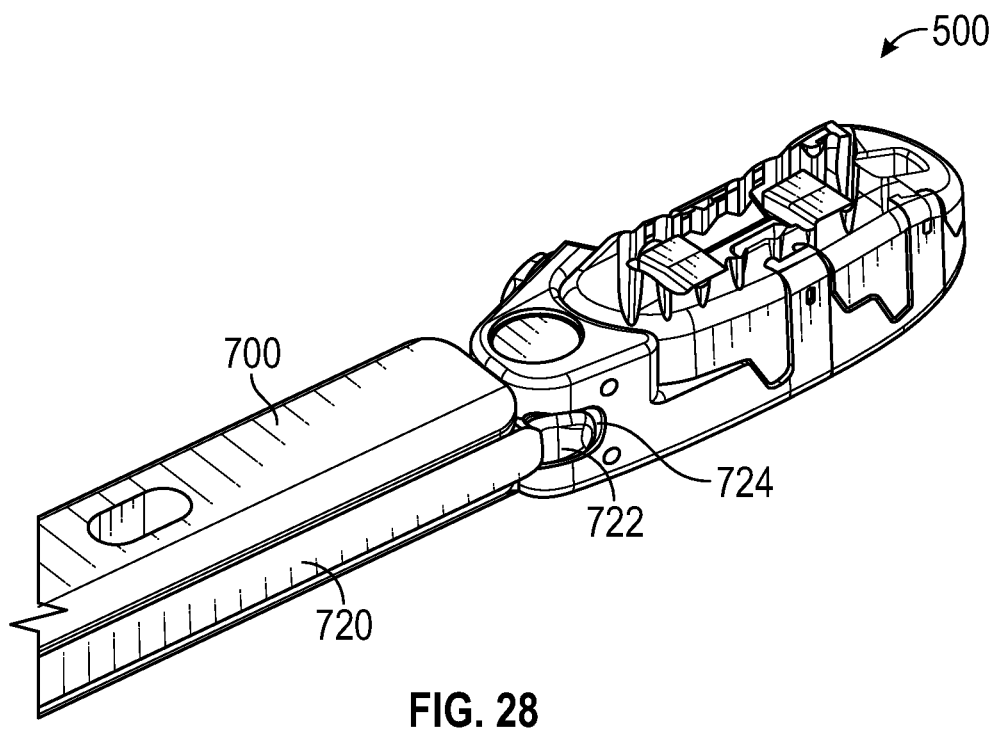
FIG. 28 is a perspective view of the tool of FIG. 27 aligning to an implant in a first configuration, according to one embodiment.
Figure 29:
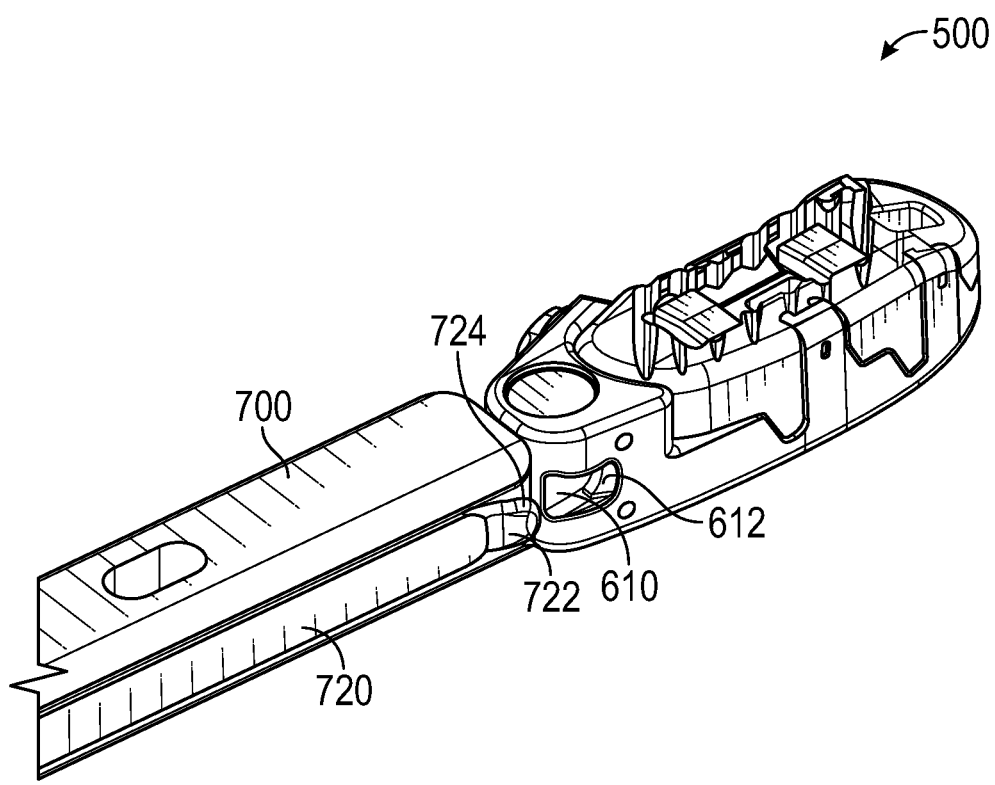
FIG. 29 is a perspective view of the tool of FIG. 27 coupled to an implant in a first configuration, according to one embodiment.
Figure 30:
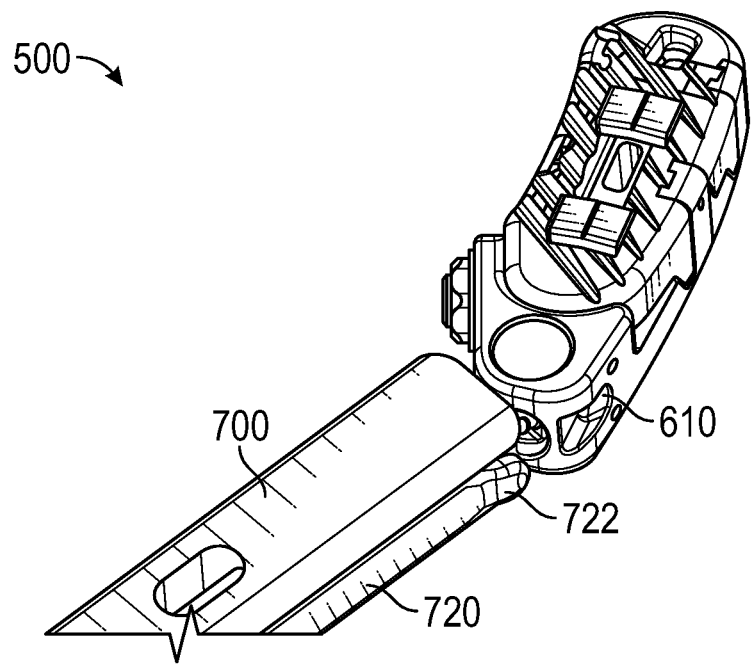
FIG. 30 is a perspective view of the tool of FIG. 27 manipulating an implant, according to one embodiment.
Figure 31:
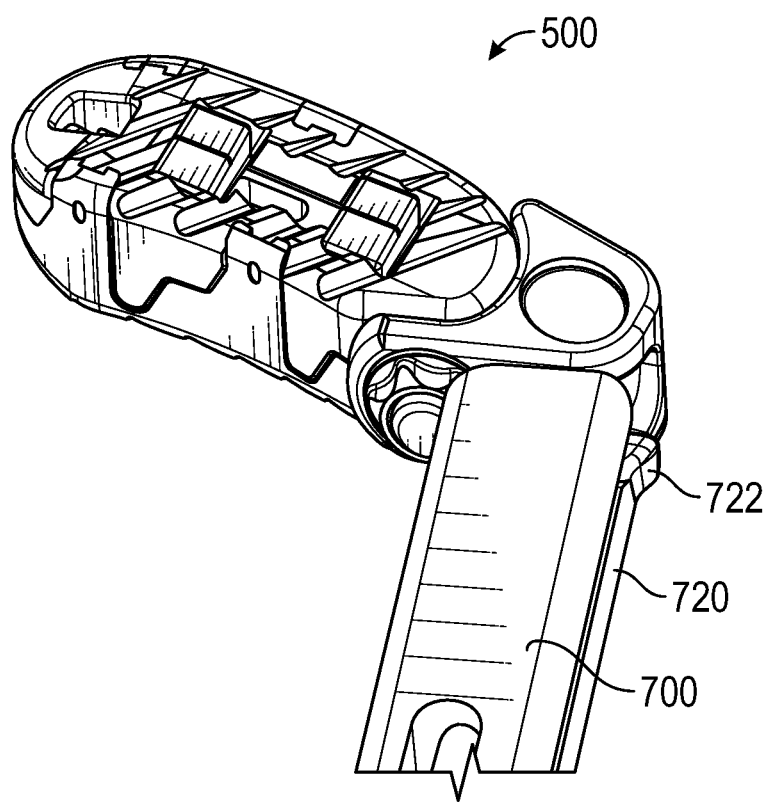
FIG. 31 is a perspective view of the tool of FIG. 27 coupled to an implant in a second configuration, according to one embodiment.
Figure 32:
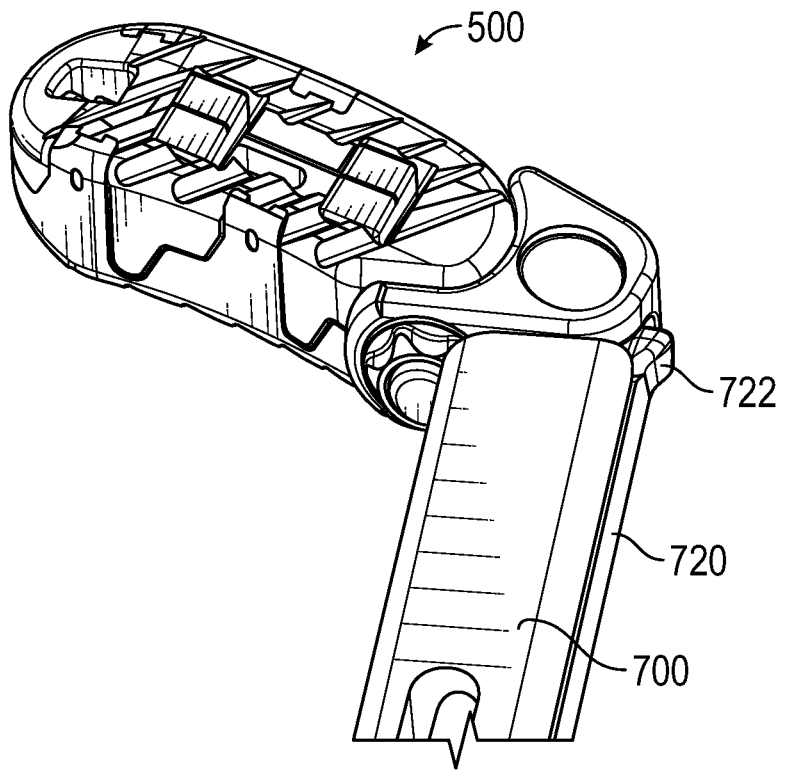
FIG. 32 is a perspective view of the tool of FIG. 27 aligning to an implant in a second configuration, according to one embodiment.
Figure 33:
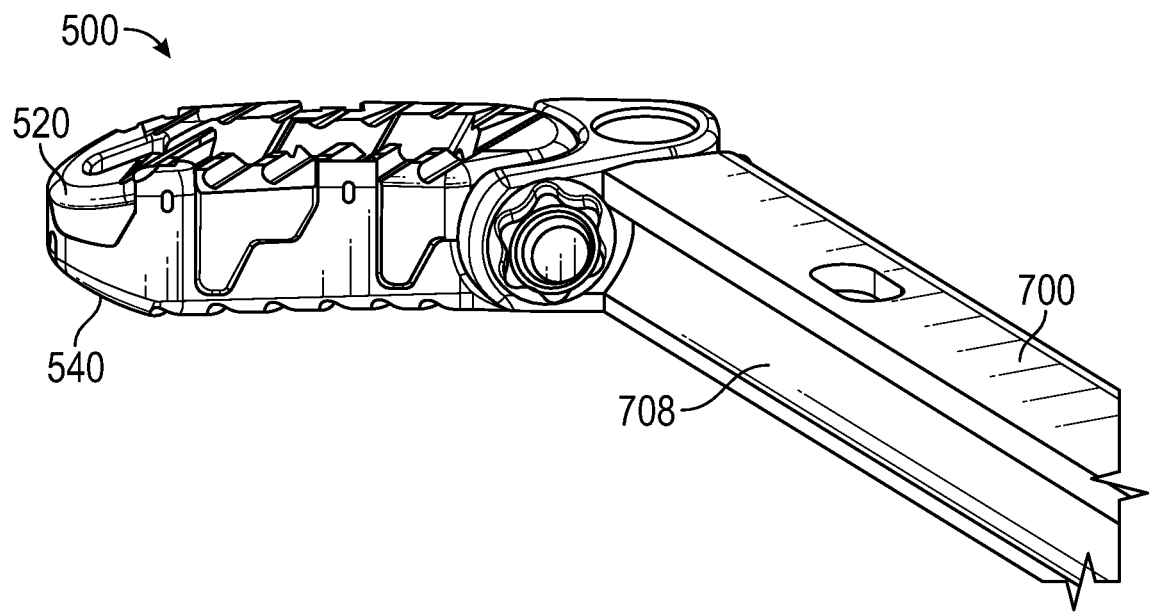
FIG. 33 is a perspective view of the tool of FIG. 27 coupled to an implant in a collapsed position, according to one embodiment.
Figure 34:
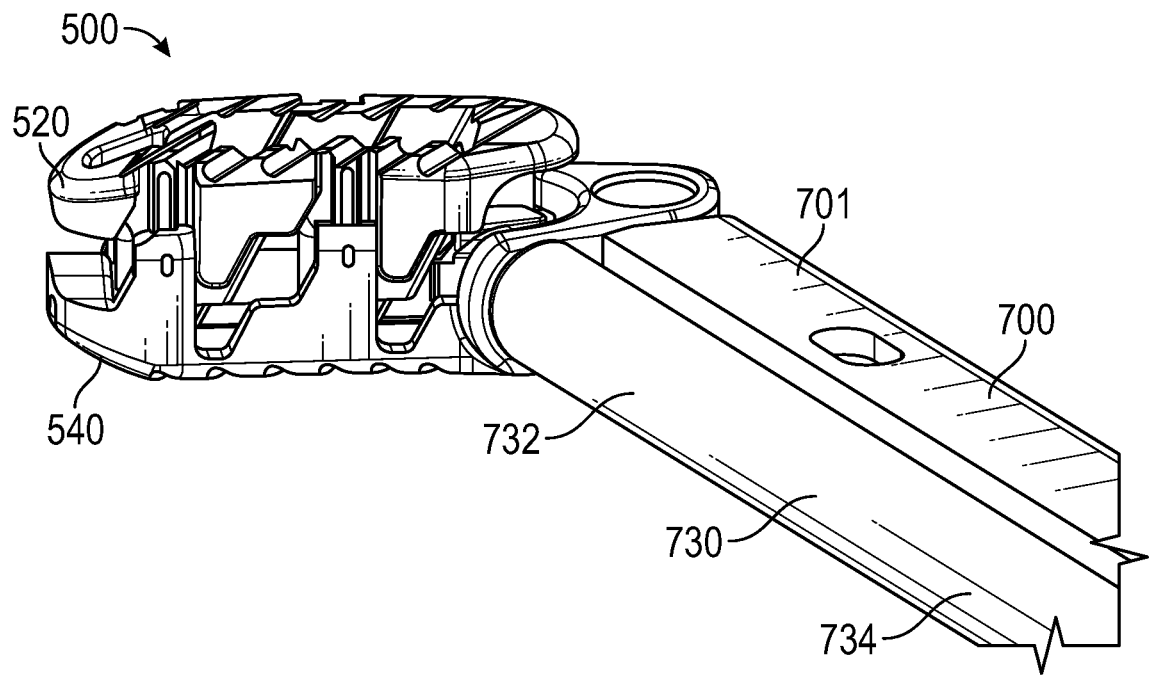
FIG. 34 is a perspective view of the tool of FIG. 27 coupled to an implant in an expanded position, according to one embodiment.

Referring now specifically to FIGS. 27-34, tool 700 for manipulation of implant 500 is shown, according to an embodiment. In brief summary, a user may operate tool 700 to manipulate a position of implant 500 and/or to expand and/or contract implant 500. FIGS. 27-28 illustrate tool 700 connecting to implant 500. FIGS. 29-31 illustrate rotation of implant 500 using tool 700. FIGS. 32-34 illustrate expansion of implant 500 using tool 700.

Referring now specifically to FIGS. 27-28, tool 700 for manipulation of implant 500 is shown, according to an exemplary embodiment. Tool 700 is shown to include first end 702 and second end 704. In various embodiments, a user operates tool 700 using second end 704. First end 702 may include coupling portion 710 configured to couple to pivot member 620. Coupling portion 710 may include threaded portion 712. Threaded portion 712 may be a male screw thread corresponding to the female threading of threaded aperture 622. A user may operate coupling portion 710 via the second end 704 to rotate the coupling portion 710 and cause tool 700 to couple to implant 500. In some embodiments, tool 700 includes aperture 706 to facilitate viewing inside tool 700. For example, a user may monitor rotation of coupling portion 710 via aperture 706. Additionally or alternatively, aperture 706 may include one or more indicators. For example, aperture 706 may include an indicator to show when tool 700 is fully coupled to implant 500. Tool 700 may further include coupling arm 720. Coupling arm 720 may be configured to align tool 700 to implant 500 and facilitate manipulation of implant 700. Coupling arm 720 includes coupling portion 722 configured to be received by coupling aperture 610. In various embodiments, coupling portion 722 includes slanted portion 724 corresponding to slanted side walls 612. For example, slanted portion 724 may be wedge shaped to facilitate axial (e.g., in and out) coupling of coupling arm 720 to coupling aperture 610 but prevent non-axial (e.g., side to side, up and down, etc.) uncoupling of the coupling arm 720 from coupling aperture 610. In one embodiment, rotation of pivot member 620 via tool 700 is prevented when coupling arm 720 is engaged with coupling aperture 610.

In various embodiments, tool 700 couples to implant 500 while pivot member 620 is in a first position. For example, an axis of threaded aperture 622 may be aligned with an axis of implant 500 and an axis of tool 700 in the first position (e.g., as shown for example in FIGS. 27-29). To attach tool 700 to implant 500, a user may align tool 700 to implant 500 using coupling arm 720 by coupling coupling arm 720 with coupling aperture 610 (e.g., by extending coupling portion 722 within coupling aperture 610). The user may then rotate coupling portion 710 to couple tool 700 to adjustable member 620.

Referring now to FIGS. 29-31, rotation of tool 700 relative to implant 500 is shown, according to an exemplary embodiment. To rotate implant 500 using tool 700, coupling arm 720 is retracted to decouple from implant 500 (e.g., FIG. 29). A user may manipulate implant 500 using tool 700 to turn pivot member 620 thereby causing rotation of implant 500. In various embodiments, tool 700 is used to rotate implant 500 from a first position to a second position. In the first position, an axis of implant 500 may be aligned with an axis of tool 700. In the second position, an axis of implant 500 may be offset from an axis of tool 700 (e.g., 60° difference, etc.). A user may align implant 500 in the second position by extending coupling arm 720 to contact coupling aperture 610 (e.g., FIG. 32).

Referring now to FIGS. 32-34, expansion of implant 500 is shown, according to an exemplary embodiment. Tool 700 is shown to include expansion member 730. In some embodiments, expansion member 730 is coupled (e.g., slideably coupled) to main body 701 of tool 700. Additionally or alternatively, expansion member 730 may be removably coupled to tool 700 such that it may contact and/or couple to tool 700 during use and decouple from tool 700 when not in use. Expansion member 730 may be configured to contact and rotate contact surface 654 and/or contact surface 644, as shown in FIG. 34. Expansion member 730 may contact an adjacent surface 708 of tool 700 configured to receive and align expansion member 730. Adjacent surface 708 may be a concave trough configured to correspond to a shape of expansion member 730. Expansion member 730 includes first end 732 and second end 734. In various embodiments, a user manipulates expansion member 730 via second end 734. First end 732 may couple to contact surface 654 to facilitate rotation thereof. For example, first end 732 may include a female recessed surface corresponding to the male raised portion of contact surface 654.

In various embodiments, a user couples expansion member 730 to contact surface 654 by extending expansion member 730 down the axis of tool 700 to contact contact surface 654. The user may manipulate expansion member 730 to rotate expansion member 730. Rotation of expansion member 730 transfers rotational force to adjustment collar 640. Rotation of adjustment collar 640 causes translation of screw 652 (e.g., in and out along axis 506). Translation of screw 652 causes surface 656 to contact translation surface 518, thereby causing horizontal translation of translation surface 518. For example, expansive rotation (e.g., rotation causing screw 652 to translate into implant 500) of expansion member 730 causes second control member 510 to translate horizontally along an axis of implant 500 in the direction of bridge 530 (e.g., away from pivot member 620) thereby causing control portions 514 and 516 to contact control channels 570 and 572 and cause expansion of adjustable member 120. Rotation of expansion member 730 may thereby cause expansion or contraction of implant 500. In various embodiments, second control member 510 operates similarly as described with reference to implant 300.

Steerable expandable implants, such as implant 100, implant 300, or implant 500, as disclosed herein, offer many advantages over traditional implants. Steerable expandable implants (e.g., implant 100, implant 300, and implant 500) may change a position of a control member (e.g., manipulation connector 202, manipulation connector 402, pivot member 620, etc.) to better orient the implant into an implantation location (i.e., a location between vertebrae of the spine). Traditional implants may have to be manually oriented for implantation. For example, an implant may be manually pushed or twisted using forceps into an implantation location, which is not conducive to microsurgery, arthroscopic surgery or the like. In addition, operation of a portion of the steerable expandable implant (e.g., manipulation connector 202, manipulation connector 402, pivot member 620) may change a position of the implant. Additionally or alternatively, operation of the portion of the steerable expandable implant may expand the implant. Traditional implants lack a single control mechanism to control multiple aspects of the implant. In contrast, the steerable expandable implants disclosed herein (e.g., implant 100, implant 300, implant 500), can control orientation and expansion of the implant from a single mechanism, reducing the complexity of implantation and the number of specialized tools required. Furthermore, the steerable expandable implants disclosed herein may be inserted in a compact orientation (e.g., laterally) to reduce the size of an insertion necessary to fit the implant before being oriented into a final orientation (e.g., horizontally) for positioning into an implantation location.

Figure 35:
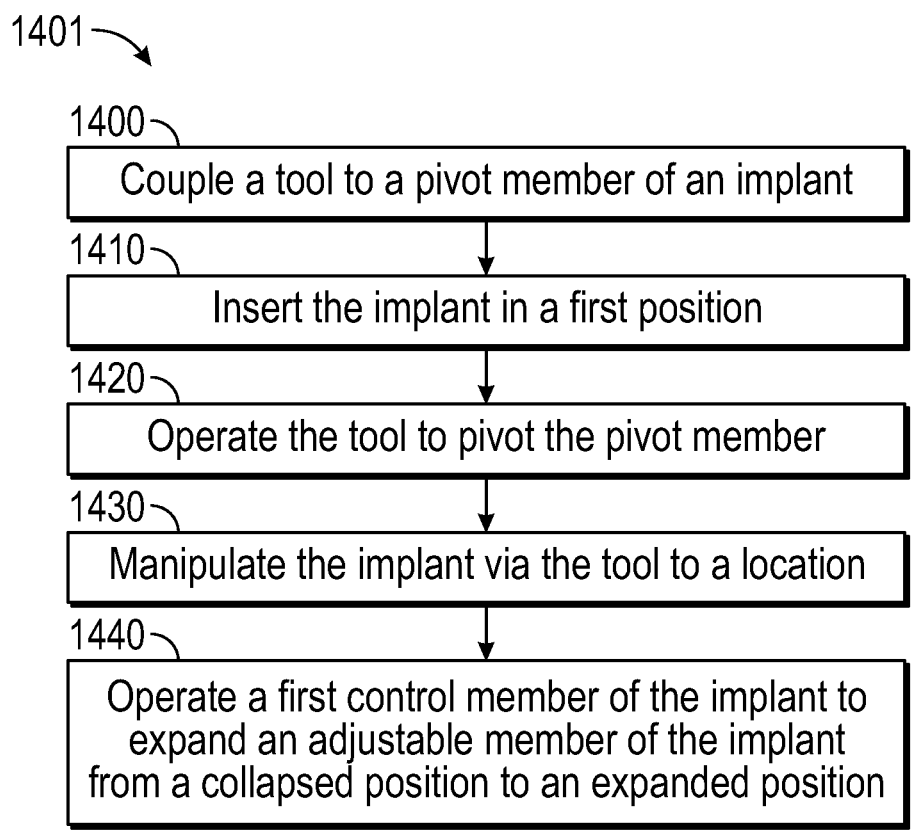
FIG. 35 is a flow chart of a process for positioning an implant, according to one embodiment.

Referring now to FIG. 35, method 1401 of positioning an implant is shown, according to an exemplary embodiment. Method 1401 may be used with the implants disclosed herein (e.g., implant 100, implant 300, implant 500 etc.), or another implant altogether. Referring now to method 1401 generally, method 1401 may be used to more easily insert and position an implant between adjacent bodies of bone. For example, method 1401 may be used to implant or insert an implant into a human spine adjacent upper and lower vertebrae of the spine.

At step 1400, a user may connect a tool to a pivot member of an implant. For example, the user may connect a manipulation device (e.g., tool 700, etc.) to a steerable control member of the implant. In some embodiments, the steerable control member is the same as or similar to the control member 200, control member 400, and/or pivot member 620. In some embodiments, the steerable control member is in a first position that configures the implant in a compact orientation. For example, the steerable control member may align the implant to be inserted lengthwise such that the implant is generally axially aligned with the manipulation device. At step 1410, the user may insert the implant into the insertion region. For example, the implant may be inserted through an incision. In some embodiments, the implant may be inserted in a first position. For example, the implant may be inserted laterally. That is, the implant may be oriented such that the smallest cross-sectional area must fit through the incision gap. In some embodiments, step 1410 roughly positions the implant before the implant is reoriented to a different orientation more convenient to positioning and manipulation.

Figure 4:
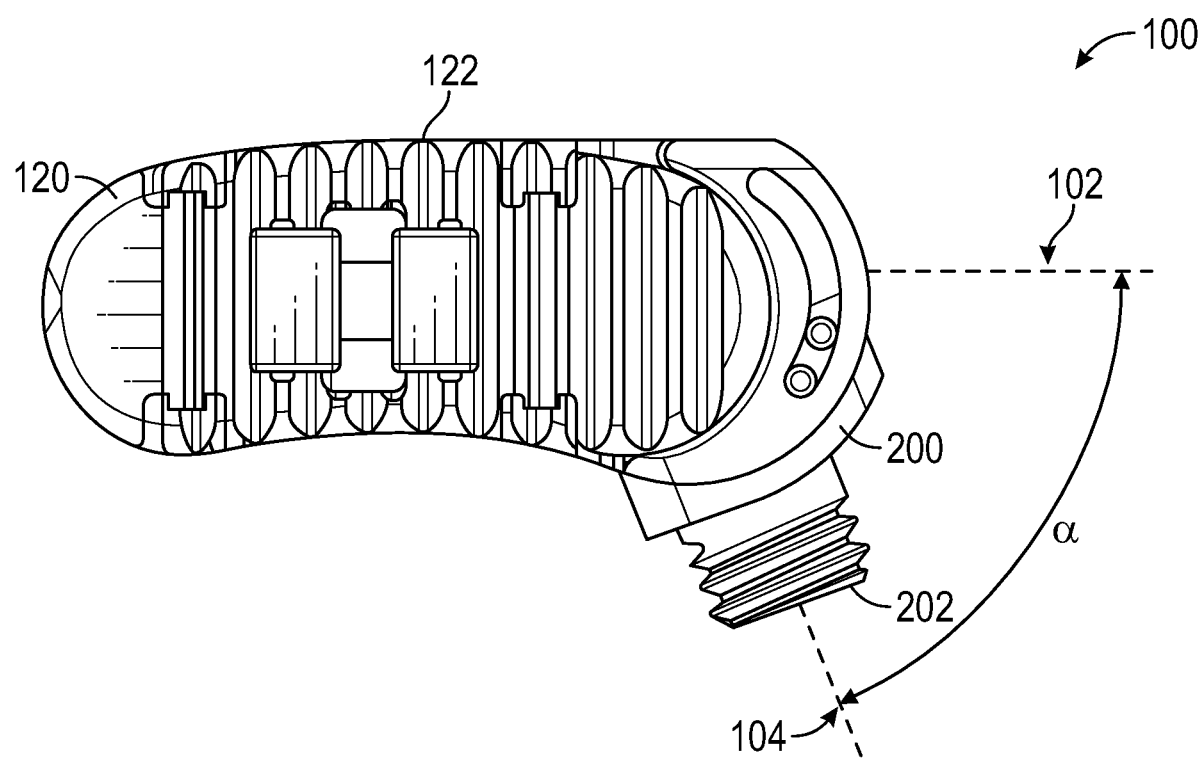
FIG. 4 is a top view of the steerable expandable implant of FIG. 1 in the second configuration, according to one embodiment.
Figure 5:
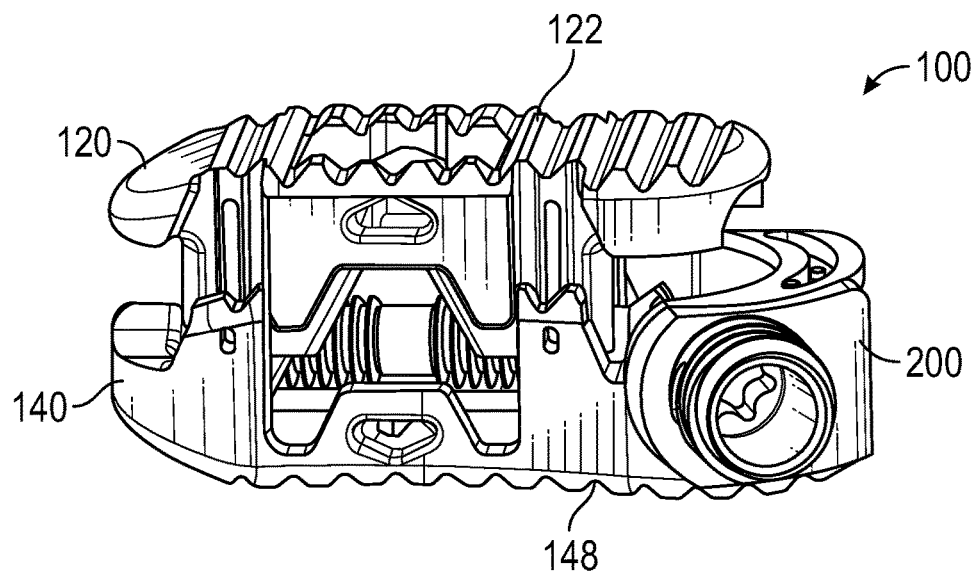
FIG. 5 is a perspective view of the steerable expandable implant of FIG. 1 in an expanded position, according to one embodiment.
Figure 6:
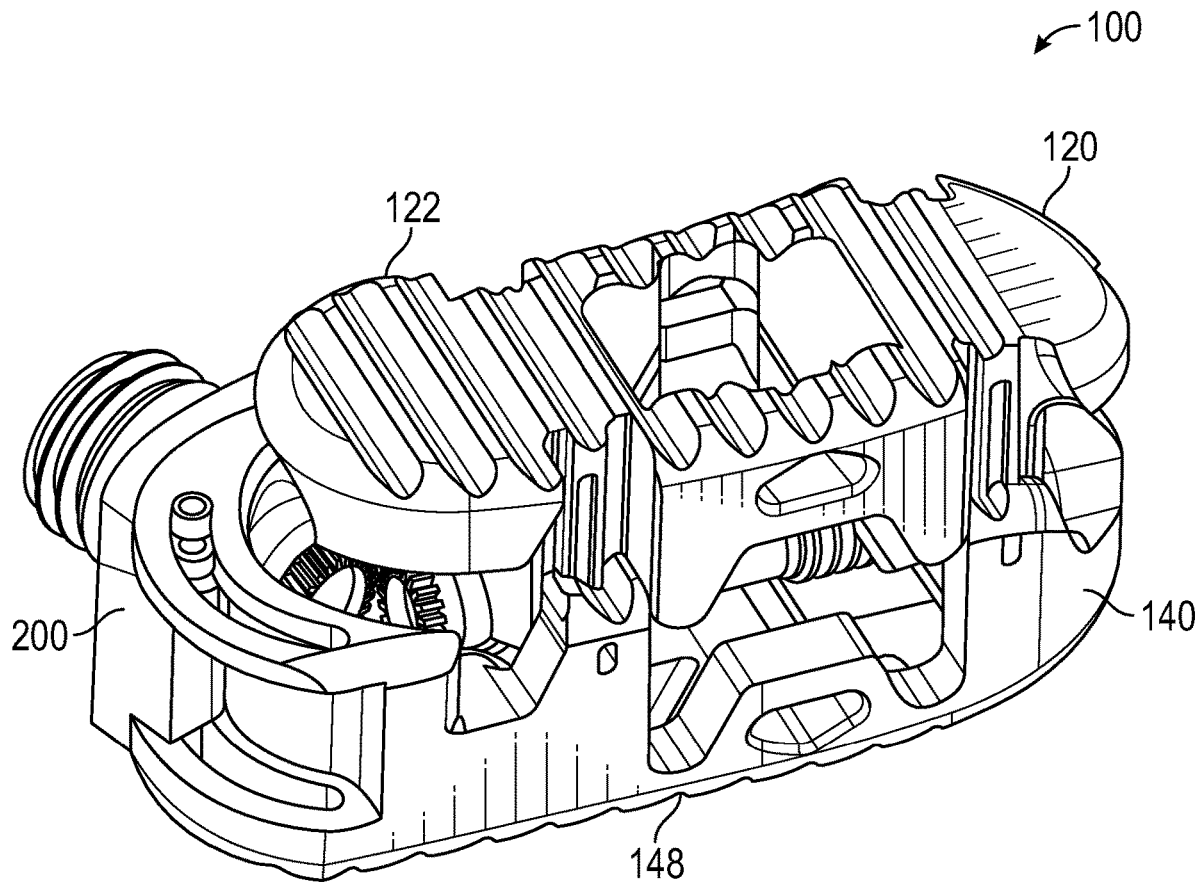
FIG. 6 is another perspective view of the steerable expandable implant of FIG. 1 in an expanded configuration, according to one embodiment.

At step 1420, the user may operate the tool to pivot the pivot member. For example, the user may operate the steerable control member of the implant to move the steerable control member to a second position. In some embodiments, the steerable control member is the same as or similar to first control shaft 130 and/or first control shaft 330. In some embodiments, the second position is such that the implant is oriented at an angle to the manipulation device for alignment with a final implantation location, as seen in FIG. 4, for example. Operation of the steerable control member may change an orientation of the implant such that the axis of the implant changes from being generally parallel with the manipulation device to being generally slanted (e.g., offset by 45°) from the manipulation device. In some embodiments, the user operates the manipulation device to move the steerable control member (e.g., control member 200, control member 400, pivot member 620) to the second position. At step 1430, the user may manipulate the implant, using the tool, to a location. For example, the user may steer the implant into an anterior position on a vertebral body of the patient. At step 1440, the user may operate a first control member (e.g., first control shaft 130, first control shaft 330, adjustment collar 640) of the implant to expand an adjustable member of the implant from a collapsed position to an expanded position. In some embodiments, the user may connect the manipulation device to the control shaft before operation. For example, the user may couple a control member of the tool to a control member of the implant. In some embodiments, the expanded position is similar to the expanded position shown in FIG. 5. In an expanded position, the implant may contact adjacent portions of bone to provide therapeutic benefits. For example, the implant may stabilize vertebra and/or promote bone grow.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. A steerable expandable implant, comprising:
   a base member configured to engage a first portion of bone;
   an adjustable member coupled to the base member and configured to engage a second portion of bone, the adjustable member movable between a collapsed position and an expanded position;
   a pivot member rotatably received by the base member and configured to receive a tool such that the tool and the pivot member are rotatable relative to the base member between a first position and a second position, wherein the pivot member is translationally fixed relative to the base member; and
   a first control member received by the base member, wherein manipulation of the first control member causes the adjustable member to move between the collapsed position and the expanded position,
   wherein the pivot member includes an aperture and wherein an axis of the aperture is angularly offset from an axis of the first control member in the first position and the axis of the aperture is angularly aligned with the axis of the first control member in the second position.

2. The steerable expandable implant of claim 1, further comprising a second control member coupled to the first control member, wherein a second axis of the second control member is aligned with the axis of the aperture when the pivot member is in the first position.

3. The steerable expandable implant of claim 2, wherein the axis of the aperture is at an angle to the second axis of the second control member when the pivot member is in the second position.

4. The steerable expandable implant of claim 2, wherein the base member further includes an alignment portion configured to receive an alignment member of the tool to position the tool relative to the base member in the first and second positions, and wherein the base member includes an alignment protrusion configured to slidably engage an alignment track of the second control member and align the second control member to the base member.

5. The steerable expandable implant of claim 1, wherein an axis of the tool is parallel to an axis of the steerable expandable implant when the pivot member is in the first position.

6. The steerable expandable implant of claim 1, wherein a top surface of a first adjustable member and a bottom surface of the base member define a height of the steerable expandable implant and are configured to engage adjacent portions of bone.

7. The steerable expandable implant of claim 1, wherein translation of the first control member changes a height of the steerable expandable implant.

8. The steerable expandable implant of claim 1, wherein a top surface of a first adjustable member and a bottom surface of a second adjustable member define a height of the steerable expandable implant and are configured to engage adjacent portions of bone, and wherein translation of the first control member changes the height of the steerable expandable implant.

9. A steerable expandable implant, comprising:
   a base member;
   an adjustable member coupled to the base member, the adjustable member movable between a collapsed position and an expanded position;
   a first control member translationally coupled and pivotally fixed relative to the base member;
   a second control member slidably coupled to the first control member and the adjustable member, wherein an axis of the second control member is angularly offset relative to an axis of the first control member; and
   a pivot member having an aperture, the pivot member rotatable between a first position and a second position, and wherein an axis of the aperture is angularly offset from the axis of the first control member in the first position and the axis of the aperture is angularly aligned with the axis of the first control member in the second position,
   wherein manipulation of the first control member causes the adjustable member to move between the collapsed position and the expanded position.

10. The steerable expandable implant of claim 9, further comprising an adjustment member threadingly coupled to the first control member, wherein rotation of the adjustment member causes movement of the first control member.

11. The steerable expandable implant of claim 9, wherein the pivot member is pivotally received by the base member and configured to receive a tool such that the tool and the pivot member are pivotable relative to the base member.

12. The steerable expandable implant of claim 11, wherein the base member further includes an alignment portion configured to receive an alignment member of the tool to align the tool to the base member.

13. The steerable expandable implant of claim 9, wherein a top surface of a first adjustable member and one of a bottom surface of the base member or a bottom surface of a second adjustable member define a height of the steerable expandable implant.

14. The steerable expandable implant of claim 13, wherein the first control member includes a first guide extending into the base member and configured to limit a range of motion of the first control member, and wherein the second control member includes a second guide extending into the base member and configured to limit a range of motion of the second control member.

15. The steerable expandable implant of claim 9, wherein the second control member includes a control portion configured to slidably align the second control member with the base member.

16. A steerable expandable implant, comprising:
   a base member;
   an adjustable member coupled to the base member, wherein the adjustable member is movable such that the steerable expandable implant may move between a collapsed position and an expanded position;
   a pivot member having an aperture, the pivot member coupled to the base member and configured to receive a tool such that the pivot member is rotatable between a first position and a second position;
   a first control member coupled to the base member; and
   a second control member slidably coupled to the first control member;
   wherein an axis of the aperture is angularly offset from an axis of the first control member in the first position and the axis of the aperture is angularly aligned with the axis of the first control member in the second position.

* * * * *